United States Patent [19]

Takanohashi et al.

[11] Patent Number: 4,695,639
[45] Date of Patent: Sep. 22, 1987

[54] THIAZOLE DERIVATIVES

[75] Inventors: Kunio Takanohashi, Kawanishi; Tsuneaki Yoshida, Osaka; Shoichiro Fujii, Nagaokakyo, all of Japan

[73] Assignee: Takeda Chemical Industries, Ltd., Osaka, Japan

[21] Appl. No.: 568,921

[22] Filed: Jan. 6, 1984

[30] Foreign Application Priority Data

Jan. 7, 1983 [WO] PCT Int'l Appl. ... PCT/JP83/00003
May 2, 1983 [WO] PCT Int'l Appl. PCT/JP83/00135

[51] Int. Cl.[4] .................. C07D 277/76; C07D 277/40
[52] U.S. Cl. .................................... 548/165; 548/190; 548/194; 548/202
[58] Field of Search ................. 548/165, 194, 190, 202

[56] References Cited

U.S. PATENT DOCUMENTS

| | | | |
|---|---|---|---|
| 4,122,258 | 10/1978 | Fujii | 544/18 |
| 4,166,115 | 8/1979 | Takaya et al. | 424/246 |
| 4,203,899 | 5/1980 | Ochiai et al. | 548/194 |
| 4,258,041 | 3/1981 | O'Callaghan et al. | 424/246 |
| 4,294,960 | 10/1981 | Takaya et al. | 544/22 |
| 4,386,210 | 5/1983 | Heymes | 548/194 |
| 4,391,979 | 7/1983 | Huwiler et al. | 548/194 |
| 4,493,933 | 1/1985 | Brodie | 548/194 |
| 4,499,088 | 2/1985 | Takaya et al. | 544/22 |

FOREIGN PATENT DOCUMENTS

| | | |
|---|---|---|
| 0048915 | 4/1982 | European Pat. Off. . |
| 0057422 | 8/1982 | European Pat. Off. . |
| 0060745 | 9/1982 | European Pat. Off. . |
| 0088853 | 9/1983 | European Pat. Off. . |
| 101148 | 2/1984 | European Pat. Off. ............. 548/194 |
| 102893 | 3/1984 | European Pat. Off. ............. 548/194 |
| 55-98189 | 7/1980 | Japan . |
| 2027691 | 2/1980 | United Kingdom . |

OTHER PUBLICATIONS

Bodansky et al., "Peptide Synthesis", 2nd Edition, (1976), John Wiley & Sons, Inc. pp. 54-56.
Kapoor, Journal of Pharmaceutical Sciences, vol. 59, No. 1, (Jan., 1970), pp. 1-27 (6-8).
Yuki Gosei Kagaku Kyokai-shi (Apr., 1968), "Diketene" pp. 311-326.
Chick et al., Journal of the Chemical Society, vol. 97 (1910) pp. 1978-2001.
Clauss, Liebigs Ann. Chem. 1980, pp. 494-502.

Primary Examiner—George F. Lesmes
Assistant Examiner—S. A. Gibson
Attorney, Agent, or Firm—Wenderoth, Lind & Ponack

[57] ABSTRACT

A novel aminothiazoleacetic acid derivative which is an advantageous synthetic intermediate for $\beta$-lactam antibiotics, and its production method and use. Starting with diketene, the production method comprises the following squence of steps.

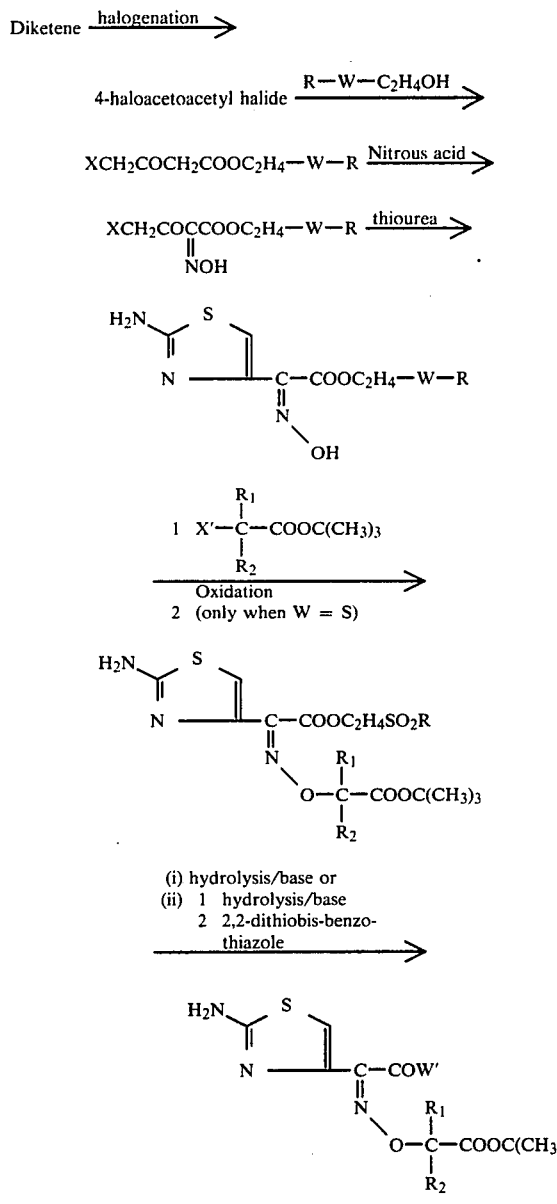

(In the above formulas, R is lower alkyl or phenyl; $R_1$ and $R_2$ each are hydrogen or lower alkyl; X and X' each are halogen; W is S or $SO_2$; and W' is OH or

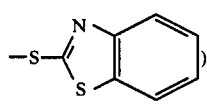

6 Claims, No Drawings

THIAZOLE DERIVATIVES

This invention relates to novel aminothiazoleacetic acid derivatives which are useful as synthetic intermediates for β-lactam antibiotics, a process for preparing the same, and a use thereof.

As synthetic intermediates useful for the production of β-lactam antibiotics having high antimicrobial activities, such as penicillins, cephalosporins, etc., there are known 2-(2-aminothiazol-4-yl)-(Z)-2-(carboxyalkyloxyimino)-acetic acid derivatives. For example, some of them have been used as the 7-side chain groups of ceftazidime, etc. which are known as the so-called third generation antibiotics, while other have been considered to be promising side chain moieties of azetidinones which are candidates of the fourth generation antibiotics. It is therefore expected that such and other 2-(2-aminothiazol-4-yl)-(Z)-2-(carboxyalkyloxyimino)-acetic acid derivatives will be utilized more often than they are today.

So far, many different processes have been proposed for the production of such 2-(2-aminothiazol-4-yl)-(Z)-2-(carboxyalkyloxyimino)-acetic acid derivatives, and among these known processes, the commercially advantageous processes may be classified into the following two major categories. One of the categories includes the method starting with an acetoacetic acid alkyl ester, which comprises oximating the ester with an alkali nitrite to an oxyiminoacetic acid ester, etherifying the oxime and, then, halogenating, and finally cyclizing the halogenation product with thiourea. The other category includes the method starting with 4-chloroacetoacetyl chloride, which comprises reacting the chloride with ethanol, butanol or the like to give a 4-chloroacetoacetic acid ester, oximating the ester with an alkali nitrite, cyclizing the oxime with thiourea to give a 2-(2-aminothiazol-4-yl)-(Z)-2-hydroxyiminoacetic acid ester, and finally etherifying the ester.

The 2-(2-aminothiazol-4-yl)-(Z)-2-(carboxyalkyloxyimino)-acetic acid derivatives thus obtained are utilized, each in the form of acid halide, acid anhydride or active amide, as acylating agents in the synthesis of β-lactam antibiotics. In this acylation reaction, it is necessary to use a 2-(2-aminothiazol-4-yl)-(Z)-2-(carboxyalkyloxyimino)-acetic acid derivative whose amino group has been protected so as to prevent occurrence of side reactions, with the result that in the synthetic processes heretofore used, 2-(2-aminothiazol-4-yl)-(Z)-2-(carboxyalkyloxyimino)-acetic acid derivatives whose amino groups have been protected are mainly synthesized. Moreover, because the carboxy group in the carboxyalkyloxyimino moiety and the carboxy group in the acetic acid moiety of such 2-(2-aminothiazol-4-yl)-(Z)-2-(carboxyalkyloxyimino)-acetic acid derivatives are more or less alike in chemical property, the carboxy group in the carboxyalkyloxyimino moiety must be protected to prevent side reactions before the derivatives are converted to reactive derivatives such as acid halides, acid anhydrides, active amides, etc. As protective groups for the carboxy group in the carboxyalkyloxyimino moiety, those groups which can be eliminated by catalytic reduction, such as p-nitrobenzyl, have been commonly employed but these groups are commercially disadvantageous in that it is difficult to remove them following the acylation reaction mentioned above. There has also been employed a tert-butyl group which is thought to be removable by acid hydrolysis but in the aforementioned second method for producing 2-(2-aminothiazol-4-yl)-(Z)-2-(carboxyalkyloxyimino)-acetic acid derivatives wherein the carboxy group in the acetic acid moiety has been mostly esterified by an alkyl group, the tert-butyl group is also eliminated during the de-esterification reaction prior to said conversion to reactive derivatives, unless the carboxyl group which is esterified with the tert-butyl group is bonded to a tertiary carbon atom. Thus, there has not been established an industrially profitable method for producing an 2-(2-aminothiazol-4-yl)-(Z)-2-(carboxyalkyloxyimino)-acetic acid derivative whose amino group and carboxy group in the acetic acid moiety have not been protected but whose carboxy group in the carboxyalkyloxyimino moiety only has been protected.

The present inventors found that in utilizing an 2-(2-aminothiazol-4-yl)-(Z)-2-(carboxyalkyloxyimino)-acetic acid derivative as an acylating agent for the synthetic production of β-lactam antibiotics, the steps of protecting the amino group prior to the acylation reaction to prevent side reactions and removing the protective group from the amino group after the acylation reaction can be omitted if the 2-(2-aminothiazol-4-yl)-(Z)-2-(carboxyalkyloxyimino)-acetic acid derivative is used in the form of an active thioester, and conducted a study to develop a commercially advantageous process for producing an 2-(2-aminothiazol-4-yl)-(Z)-2-(carboxyalkyloxyimino)-acetic acid derivative of which the amino group and the carboxy group in the acetic acid moiety are unprotected and the carboxy group in the carboxyalkyloxyimino moiety is protected. It was, found, surprisingly, that among the various conceivable combinations of reaction steps, the following process provides a novel aminothiazoleacetic acid derivative of the formula

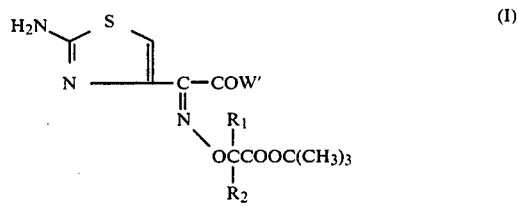

wherein $R_1$ and $R_2$ each are a hydrogen atom or a lower alkyl group, and W' is hydroxyl or 2-benzothiazolylthio, or a salt thereof in good yield. Thus, this process comprises reacting diketene with a halogen and then with a β-lower alkyl- or phenyl-thio- or sulfonyl-ethanol, oximating the reaction product with nitrous acid or a salt thereof, reacting it further with thiourea or a salt thereof, etherifying the oxime, if necessary oxidizing the same, and finally eliminating the protective group for the carboxy group in the acetic acid moiety. This process permits easy and selective removal of the protective group from said carboxy group in acetic acid moiety. It was further found that the compound (I) wherein W' is OH thus obtained can be reacted with 2,2-dithiobis-benzothiazole to produce an active thioester, i.e. the compound (I) wherein W' is 2-benzothiazolylthio, which is an advantageous synthetic intermediate for β-lactam antibiotics. The present invention is based on the above findings.

Thus, this invention relates to an aminothiazoleacetic acid derivative (I), a use of the derivative (I) as an intermediate for the synthetic production of β-lactam antibiotics, and a process for preparing the derivative (I) characterized by:

reacting diketene with halogen;
reacting the resulting 4-haloacetoacetyl halide with an alcohol of formula (II):

R—W—C₂H₄OH    (II)

wherein R is lower alkyl or phenyl; and W is S or SO₂;
reacting the resulting compound of formula (III):

XCH₂COCH₂COOC₂H₄—W—R    (III)

wherein X is a halogen atom; and R and W are as defined above with nitrous acid or a salt thereof;
reacting the resulting compound of formula (IV):

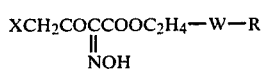

XCH₂COCCOOC₂H₄—W—R    (IV)
       ‖
       NOH wherein
the symbols are as defined above, with thiourea or a salt thereof;
reacting the resulting compound of formula (V):

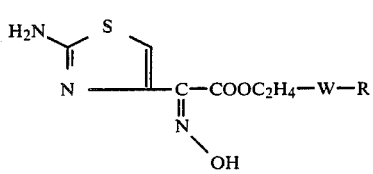

(V)

wherein the symbols are as defined above or a salt thereof, with a compound of formula (VI):

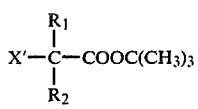

R₁
         |
X'—C—COOC(CH₃)₃    (VI)
         |
         R₂ wherein X' is a halogen atom; and other symbols are as defined above, to produce a compound of formula (V')

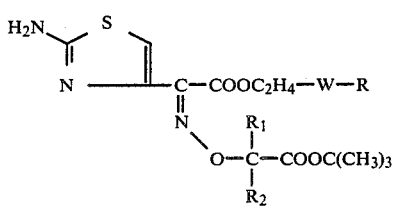

(V')

wherein the symbols are as defined above, or a salt thereof;
oxidizing further the reaction product (V') or a salt thereof when W is S; and (i) hydrolyzing the resulting compound of formula (VII):

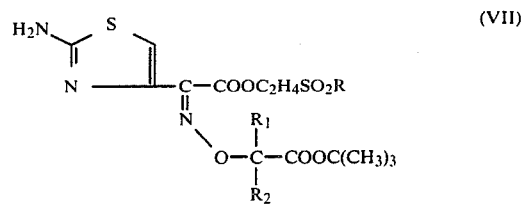

(VII)

wherein the sybmols are as defined above, or a salt thereof, in the presence of a base, to obtain the derivative (I) wherein W' is OH or (ii) hydrolyzing the compound (VII) or a salt thereof in the presence of a base, and reacting the obtained derivative (I) wherein W' is OH with 2,2-dithiobis-benzothiazole to obtain the derivative (I) wherein W' is 2-benzothiazolylthio.

Referring to the above formulas, R₁ and R₂ are the same or different and each represents hydrogen or lower alkyl. The lower alkyl group R₁ or R₂ may be a group containing 1 to 4 carbon atoms, such as methyl, ethyl, propyl, isopropyl, butyl, isobutyl, sec-butyl, tert.-butyl, etc. Preferred are the cases in which both R₁ and R₂ are hydrogen or methyl, or one of R₁ and R₂ is hydrogen and the other methyl. R is lower alkyl or phenyl. The lower alkyl R may for example be a C₁₋₄ lower alkyl as mentioned for R₁ and R₂. Preferred examples of R are methyl and ethyl. The halogen X, X' may for example be chlorine, bromine, iodine or fluorine. X and X' may be the same halogen or different halogens. Frequently used examples of X and X' are chlorine and bromine. W stands for S or SO₂. W' is OH or

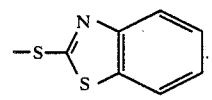

In the method according to this invention, diketene is reacted with a halogen in the first place to give a 4-haloacetoacetyl halide. In this step, diketene may be reacted with an equimolar or slightly less than equimolar amount of a halogen under cooling. This reaction may be conducted in a solvent. As the solvent, a halogenated hydrocarbon such as methylene chloride, chloroform, etc., an ester such as ethyl acetate, etc., or an ether such as ether, dioxane, etc., for instance, may be employed. The reaction may be conducted under cooling, i.e. from −70° C. to 10° C. The reaction time may be very short and generally the reaction may go to completion substantially upon completion of addition of the halogen. It may be, therefore, sufficient to stir the reaction system for about 30 minutes after addition of the halogen. The resulting 4-haloacetoacetyl halide can be separated and purified by the conventional procedure, e.g. concentration, solvent extraction, pH adjustment, crystallization, chromatography, etc., but it is advantageous to submit the reaction mixture as such to the next reaction step.

The 4-haloacetoacetyl halide is then reacted with alcohol (II) to give compound (III).

In this step, the 4-haloacetoacetyl halide is preferably reacted with an equivalent or slightly less than equivalent amount of alcohol (II). This reaction may be conducted in a solvent. The solvent may be any solvent that does no interfere with the reaction, and may be preferably a halogenated hydrocarbon such as methylene chloride, chloroform, carbon tetrachloride, etc. or an ether such as tetrahydrofuran, dioxane, diethyl ether, etc., for instance. Further, this reaction is preferably carried out in the presence of a base. As such a base, there may, for example, be employed aromatic amines such as pyridine, picoline, N,N-dimethylaniline, etc. and aliphatic tertiary amines such as trimethylamine, triethylamine, etc. The amount of the base is about 1-3 moles per mole of alcohol (II). Generally, the reaction may be conducted under cooling or at room temperature (at $-20°$ to $40°$ C.). The reaction generally goes to completion in tens of minutes to a few hours. The resulting 4-haloacetoacetic acid ester (III) can be purified by the conventional purification procedure such as distillation, phasic transfer, recrystallization, etc. but since this reaction proceeds in high yield, the reaction mixture may be submitted to the next reaction step without prior purification.

The 4-haloacetoacetic acid ester (III) is then reacted with nitrous acid or a salt thereof to give the oxime.

The reaction is generally carried out using compound (III) and nitrous acid in an approximately equimolar ratio, although nitrous acid may be used in slight excess. While nitrous acid may be used as it is, it can be used as a salt with an alkali metal such as sodium or potassium, for instance. The reaction may proceed in a solvent. The reaction temperature may be under cooling or at room temperature (at $-50°$ to $50°$ C., preferably $-10°$ to $40°$ C.). The solvent used for this reaction may for example be an ether, e.g. tetrahydrofuran, dioxane, diethyl ether, etc., a fatty acid such as glacial acetic acid, or a mixture thereof. The amount of water which may be added to such solvent is virtually optional. As an alternative, an aqueous solution of nitrite (e.g. sodium nitrite) may be added to consequently introduce water into the reaction system. The reaction time depends on the amounts of starting compounds, the solvent, etc. The reaction may go to completion in a very short time (20 minutes to 3 hours). The product oxime (IV) can be purified by the known procedure such as distillation, solvent extraction, concentration, recrystallization, etc., but it is generally unnecessary to purify it but the reaction mixture as such may be used as the reactant for the next step.

The compound (V) or a salt thereof can be produced by reacting this oxime compound (IV) with thiourea or a salt thereof.

Generally, each mole of compound (IV) is reacted with one mole or a slight excess of thiourea or a salt thereof, although thiourea may be used in larger excess unless the reaction is not thereby adversely affected. As a salt of thiourea, there may, for example, be a salt with an inorganic acid such as hydrochloric acid, hydrobromic acid, sulfuric acid, phosphoric acid, etc. This reaction is generally conducted in a solvent. The solvent is preferably a mixture of water with a water-miscible solvent such as an alcohol, e.g. methanol, ethanol, etc., a ketone, e.g. acetone, diethyl ketone, etc., an ether e.g. tetrahydrofuran, dioxane, diethyl ether, etc., an acid amide, e.g. N,N-dimethylformamide, N,N-dimethylacetamide, etc., or an organic amine, e.g. N-methylpiperidone, etc. Furthermore, the syn-isomer (V) is selectively produced when the reaction is conducted in the presence of a basic reagent. The basic reagent used for this reaction may be an alkali metal or alkaline earth metal salt of a lower aliphatic carboxylic acid, or an inorganic or organic base having a pKa value of 9.5 or more, preferably a pKa value of 9.8 to 12.0. Examples of the lower aliphatic carboxylic acid salt include salts of lower aliphatic carboxylic acids containing 1 to 6 carbon atoms, e.g. sodium acetate, potassium acetate, calcium acetate, barium acetate, sodium formate, sodium propionate, potassium hexanoate, etc. The inorganic base may for example be a carbonic acid alkali metal salt such as sodium carbonate, potassium carbonate, etc. While, the organic base is exemplified by tri-lower ($C_{1-4}$)alkyl-substituted amines such as trimethylamine, triethylamine, tributylamine, etc. and N-lower ($C_{1-2}$)alkyl-substituted 5- to 6-membered cyclic amines such as N-methylpyrrolidine, N-ethylpyrrolidine, N-methylpiperazine, N-ethylpiperazine, etc. When any of said N,N-dimethylformamide, N,N-dimethylacetamide and N-methylpyrrolidone is used as the solvent, the above-mentioned base may not necessarily be added. While the addition level of such base depends on the kinds of starting material and solvent, it may range from 0.5 to 1.5 moles per mole of compound (IV). The reaction is generally conducted to $0°$ to $40°$ C., although the reaction system may be cooled to warmed to control the reaction rate. The reaction may to completion in 10 minutes to 4 hours. The resulting compound of formula (V) can be separated and purified by the conventional procedure such as distillation, pH adjustment, crystallization, recrystallization, etc. When the anti-isomer is included as an impurity, it can be separated by the conventional procedure such as fractional crystallization, chromatography, etc. Since compound (V) has basic amino group in 2-position of the thiazole ring, it may be converted to the salt with an organic acid such as acetic acid, tartaric acid, methanesulfonic acid, etc., an inorganic acid such as hydrochloric acid, hydrobromic acid, sulfuric acid, phosphoric acid, etc. or an acidic amino acid such as arginine, aspartic acid, glutamic acid, etc. by the conventional procedure and isolated as such salt.

The compound (V) or a salt thereof is then reacted with compound (VI) and, if W is S, the reaction product is further oxidized to a compound of formula (VII) or a salt thereof.

The compound (V) may be one having a free amino group or one in which the amino group has formed a salt with one of the acids as mentioned above. Theoretically, one molar equivalent of compound (VI) may be reacted with one equivalent of compound (V) or a salt thereof. Usually, however, 1.5 to 2.0 equivalents of compound (VI) may be used per mole of compound (V) or a salt thereof. This reaction is conducted in a solvent.

The solvent is preferably a ketone such as acetone, methyl ethyl ketone, etc. or a nitrile such as acetonitrile, propionitrile, etc.

A base may be added to the reaction system for the purpose of conducting the reaction advantageously. The base may be any base that will promote the reaction and is preferably an alkali carbonate such as potassium carbonate, sodium carbonate, sodium hydrogen carbonate, etc. The amount of such base may be 1.5 to 10 molar equivalents, preferably 1.5 to 5 equivalents, based on starting compound (V). For a smooth conduct of the reaction, it is preferable to add water to the reaction system, and particularly to the solvent, and the addition level of water may be 0.1 to 2% by volume, preferably 0.5 to 1.5% by volume, relative to the solvent. The reaction temperature may be $10°$ to $60°$ C. and preferably $20°$ to $50°$ C. Under these conditions the reaction proceeds quantitatively and the starting materials disappear in 0.5 to 3 hours. Thus, the reaction may be completed at this time point. After completion of the reaction, the desired syn-isomer (V') can be separated and purified by the conventional procedure such as extraction, pH adjustment, chromatography, etc.

When W of compound (V) is S, the resulting compound of the formula [i.e. the formula (V') wherein W is S]:

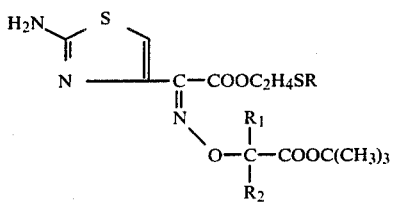 (VII')

wherein the symbols are as defined hereinbefore, is further oxidized to compound (VII). This oxidation of sulfide to sulfone is conducted using an oxidizing agent such as hydrogen peroxide, ozone or a peracid (e.g. sodium metaperiodate, perbenzoic acid, etc.). Among others, hydrogen peroxide, etc. is employed. The reaction may be readily accelerated by adding a catalyst to such oxidizing agent.

For example, when hydrogen peroxide is used as the oxidizing agent, the addition of a catalytic amount of ammonium molybdate, sodium tungustate or the like accelerates the reaction. The amount of oxidizing agent may be 2 to 15 molar equivalents, preferably 2 to 7 equivalents, relative to the sulfide. This reaction may be conducted at 0° to 40° C., and preferably at room temperature. The reaction may go to completion in 2 to 7 hours. This reaction is conducted in a solvent. As the solvent, there may be employed a hydrophilic solvent such as acetone, acetonitrile, glacial acetic acid, etc., for instance, and these solvents may be used in admixture with water.

The resulting sulfone (VII) can be separated and purified by the conventional procedure such as extraction, crystallization, chromatography, etc. However, since this reaction is substantially not accompanied by side reactions, the reaction mixture may be directly submitted to the next reaction step, i.e. hydrolysis under alkaline conditions, on completion of the oxidation reaction.

The compounds (V'), (VII') and (VII), as well as compound (V), have an amino group in 2-position of the thiazole ring and, therefore, can be converted to a salt such as those mentioned for compound (V) before isolation. However, the reaction mixture as such is preferably submitted to the next hydrolysis step without separation of compound (VII) or a salt thereof.

The compound (VII) or a salt thereof prepared as above is then hydrolyzed in the presence of a base to give the desired compound (I) wherein W' is OH or a salt thereof. While it is more convenient to use the reaction mixture from the synthesis of (VII) than to employ the isolated compound (VII), the latter may of course be employed either as a free compound or in the form of salt referred to above. Hydrolysis of compound (VII) or a salt thereof may be conducted by permitting a base to act on (VII) or a salt thereof. The hydrolysis may be conducted a hydrophilic solvent. Water may be added to accelerate the reaction. When a base was employed in the synthesis of (VII), the addition of water alone to the reaction mixture causes hydrolysis to take place in succession to the formation of (VII). The hydrophilic solvent may for example be an alcohol, e.g. methanol, ethanol, etc.; a ketone, e.g. acetone, etc.; or a nitrile, e.g. acetonitrile. The amount of the solvent may be 2 to 50 volumes, preferably 5-10 volumes, relative to the compound (VII). The amount of water to be mixed with such solvent may be 0.5 to 10 volumes, relative to the solvent. The hydrolysis temperature is preferably 5° to 50° C. The base may be any one showing pH ranging from about 9 to 12, and may for example be an alkali carbonate such as potassium hydrogen carbonate, potassium carbonate, etc. or an organic amine such as triethylamine, isopropylamine, etc. The amount of the base is preferably one molar equivalent to about 5 equivalents, relative to the compound (VII) or a salt thereof and the hydrolysis generally may go to completion in 30 minutes to 2 hours. The resulting compound (I) wherein W' is OH can be separated and purified by the conventional procedure mentioned hereinbefore. However, the reaction mixture as such may be submitted to the next step without separation of the compound (I) wherein W' is OH. The product compound (I) wherein W' is OH can be converted to an acid salt at the 2-amino group of the thiazole ring just as mentioned for compounds (V) and (VII), and because it has a carboxy group, can also be converted to the salt of an alkali metal such as sodium, potassium, etc. or an alkaline earth metal such as calcium, magnesium, etc. by the conventional procedure.

The product compound (I) wherein W' is OH thus obtained can be easily converted to an active thioester at the carboxy group thereof, i.e. the compound (I) wherein W' is

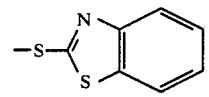

and can be used as an advantageous acylating agent in the synthesis of β-lactam antibiotics. In this application, the steps of protecting the amino group prior to the acylation reaction to prevent side reactions and removing the protective group for the amino group after the acylation reaction, which are necessary in the conventional method for producing the β-lactam antibiotics, can be omitted.

The compound (I) wherein W' is

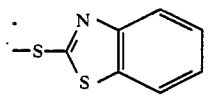

is produced by reacting the compound (I) wherein W' is OH with 2,2-dithiobis-benzothiazole. 2,2-Dithiobis-benzothiazole may be used in an amount of 1 to 4 moles per mole of (I) wherein W' is OH. The reaction may be conducted in an inactive organic solvent having no hydroxy group in its molecule. A phosphine or phosphite may be added to the reaction system to accelerate the reaction. As such a phosphine, use may be made of aryl phosphines such as triphenyl phosphine, and as such a phosphite, use may be made of tri-lower alkyl phosphites such as trimethyl phosphite or triethyl phosphite. The phosphine or phosphite is preferably used in an amount of 1 to 2 moles per 1 mole of (I) wherein W' is OH. The inactive organic solvent to this reaction includes halogenated hydrocarbons such as dichloromethane, chloroform, etc., nitriles such as acetonitriles, propionitrile, etc., esters such as ethyl acetate, isopropyl acetate, etc. Among them, nitriles such as acetonitrile, for instance, are especially preferable. The amount of the solvent may be 10–50 times (weight) of that of the compound (I) wherein W' is OH. In order to dissolve (I) wherein W' is OH, a base may be added to the solvent. For example, an organic base such as pyridine, N-methylmorpholine, triethylamine, etc. may be used as the base. The amount of the base may be 1–2.5 moles per 1 mole of (I) wherein W' is OH. The reaction temperature is normally −30° C.–50° C., preferably −20° C.–25° C., more preferably −5° C.–5° C. The reaction time is usually about 1–20 hours. Generally, thus obtained compound (I) wherein W' is 2-benzothiazolylthio

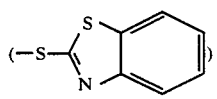

forms precipitation and so may be isolated by filtration. If necessary, before the filtration, putting the obtained reaction mixture into water, extracting the aqueous solution with such an organic solvent as mentioned above and then adding n-hexane, etc. to the extract in this order may be conducted to get the compound (I) wherein W' is 2-benzothiazolylthio as precipitates. Thus, e.g. 2-(2-aminothiazol-4-yl)-(Z)-2-(t-butoxycarbonylmethoxyimino)-acetic acid or 2-(2-aminothiazol-4-yl)-(Z)-2-(1-t-butoxycarbonyl-1-methylethoxyimino)-acetic acid may be converted to a 2-benzothiazolethio ester, then the latter may be reacted with 7-amino-3-pyridinomethyl-3-cephem-4-carboxylate, and finally the protective group for the carboxy group may be eliminated in the conventional manner to give 7-[2-(2-aminothiazol-4-yl)-(Z)-2-(carboxymethoxyimino)acetamido]-3-pyridinomethyl-3-cephem-4-carboxylate or ceftazidime (U.S. Pat. No. 4,258,041).

In practicing the above method, 7-amino-3-pyridinomethyl-3-cephem-4-carboxylate is reacted with the 2-benzothiazolethio ester in proportion of 1 mole of the former to at least 1 mole, preferably 1–4 moles of the latter. The reaction may be carried out in a solvent. The solvent includes water, acetone, dioxane, acetonitrile, methylene chloride, chloroform, dichloroethane, tetrahydrofuran, ethyl acetate, N,N-dimethylformamide, N,N-dimethylacetamide, pyridine and other common organic solvents inert to the reaction. Hydrophilic solvents may be used in admixture with water. The reaction may also be conducted in the presence of such a base as an alkali metal carbonate, a trialkylamine (e.g. trimethylamine, triethylamine, tributylamine), N-methylmorpholine, N-methylpiperidine, N,N-dialkylaniline, N,N-dialkylbenzylamine, pyridine, picoline, lutidine, 1,5-diazabicyclo(4,3,0)-non-5-ene, 1,4-diazabicyclo(2,2,2)octane or 1,8-diazabicyclo(5,4,4)un-decene-7. When the base is a liquid, it may also serve as the solvent. A preferable solvent is a halogenated alkane such as methylene chloride, etc., and as a base, for example, an trialkylamine such as trimethylamine, etc. is advantageously used. The reaction temperature is not critical but, generally, the reaction is carried out in many cases with cooling or at room temperature. The reaction is complete in several minutes to a few scores of hours. The reaction temperature and time are 0°–40° C. and a few minutes to several hours, respectively, to gain a good result. The protective group for the carboxyl group of thus obtained compound may be removed in the conventional manner, e.g. acid or base catalysed hydrolysis. The reaction product can be recovered and purified by per se known methods, such as concentration, pH adjustment, phase transfer, solvent extraction, crystallization, recrystallization, fractional distillation and chromatography.

And, in the same manner as mentioned above, the 2-benzothiazolethio ester of 2-(2-aminothiazol-4-yl)-(Z)-2-(t-butoxycarbonylmethoxyimino)-acetic acid may be reacted with 7-amino-3-methylthiomethyl or [(5-methyl-1,3,4-thiadiazol-2-yl)thiomethyl]-3-cephem-4-carboxylic acid, and then the protective group of the carboxyl group in the t-butoxycarbonylmethoxyimino moiety may be removed to produce disodium 7β-[2-(2-aminothiazol-4-yl)-(Z)-2-(carboxymethoxyimino)acetamido]-3-methylthiomethyl-3-cephem-4-carboxylate [Compound (A)], or disodium 7β-[2-(2-aminothiazol-4-yl)-(Z)-2-(carboxymethoxyimino)-]acetamido-3-[(5-methyl-1,3,4-thiadiazol-2-yl)thiomethyl]-3-cephem-4-carboxylate [Compound (B)]. Thus obtained compounds (A) and (B) show excellent activity against a broad spectrum of bacteria inclusive of gram-negative bacteria, such as *Escherichia coli, Serratia marcescesn, Proteus rettgeri, Enterobacter cloacae* and *Citrobacter freundii*, and are resistant to β-lactamase. The Compounds (A) and (B) may be used, for example as a disinfectant for removing the aforesaid microorganisms from surgical instruments or as an anti-infective agent. When the Compounds (A) and (B) are employed as an antiinfective agent, for example for the treatment of intraperitoneal infections, respiratory organ infections, urinary tract infections and other infectious deseases caused by the aforementioned microorganisms, it may be safely administered to mammals including humans, mice and rats at a daily dose level of 0.5 to 80 mg per kilogram body weight, preferably 1 to 20 mg on the same basis, in 3 to 4 installments daily. The compounds (A) and (B) may be administered orally or parenterally in varied dosage forms such as injections, capsules, powders, granules and tablets which may be manufactured by established or known arts. Where the compound (A) or (B) is used as an injection, the carrier may for example be distilled water or physiological saline. In the case the compound (A) or (B) is used as a capsule, powder, granules or tablet, the compound (A) or (B) is employed, for example in admixture with pharmacologically acceptable, per se known excipients (e.g. starch, lactose, sucrose, calcium carbonate, calcium phosphate), binders (starch, gum arabic, carboxymethyl-cellulose, hydroxypropylcellulose, crystalline cellulose, etc.), lubricants (e.g. magnesium stearate, talc, etc.), and disintegrating agents (e.g. carboxymethyl calcium, talc, etc.).

The following working and reference example are further illustrative of this invention. In these examples, NMR spectra were determined with a Varian T60 spectrometer (60 MHz) [manufactured by Varian Analytical Instrument Division in U.S.A.] using tetramethylsilane as a reference and the δ values are expressed in ppm. In the spectra, s represents a singlet, d a doublet, t a triplet, q a quartet, m a multiplet, J a coupling constant, DMSO dimethyl sulfoxide, br. broard, and arom. aromatic.

EXAMPLE 1

In 260 ml of methylene chloride was dissolved 87.9 g (1.407 moles) of diketene. The solution was cooled to −35° C. and 74.2 g (1.045 moles) of chlorine gas was bubbled into the solution at −35° to −30° C. for about 2 hours to prepare a methylene chloride solution of 4-chloroacetoacetyl chloride. Separately, 100 g (0.805 mole) of methylsulfonylethanol was dissolved in 130 ml of methylene chloride followed by addition of 63.7 g of pyridine. To this solution was added the above methylene chloride solution of 4-chloroacetoacetyl chloride at −5° to 0° C. dropwise over a period of about 1.5 hours. The mixture was then stirred for 30 minutes and poured in water, and 800 ml of methylene chloride was added to extract the reaction product. The water layer was further extracted with methylene chloride and the organic layers were combined and washed with water. The organic solution was concentrated to dryness and the concentrate was dissolved in 50 ml of methylene chloride and crystallized by addition of 200 ml of isopropyl ether to give 156.3 g (yield: 80% based on methylsulfonylethanol) of methylsulfonylethyl 4-chloroacetoacetate as white crystals.

NMR (60 MHz, CDCl$_3$) δ: 3.00 (3H, s, SO$_2$C$\underline{H}_3$), 3.38 (2H, t, J=7 Hz, —C$\underline{H}_2$SO$_2$—), 3.72 (2H, s, COC$\underline{H}_2$CO) 4.25 (2H, s, ClC$\underline{H}_2$CO), 4.60 (2H, t, J=7 Hz, COC$\underline{H}_2$CH$_2$).

IR$\nu_{max}^{KBr}$ cm$^{-1}$: 3430, 1745, 1730.

EXAMPLE 2

In 315 ml of glacial acetic acid was suspended 156.3 g (0.644 mole) of methylsulfonylethyl 4-chloroacetoacetate as obtained in Example 1. The suspension was cooled to 5° C. or below and a solution of 44.4 g (0.644 mole) of sodium nitrite in 140 ml of water was added at 0°–5° C. over a period of about 2 hours. The mixture was stirred for 30 minutes, poured in ice water and extracted with ethyl acetate. The organic layer was washed with water and dried over anhydrous sodium sulfate. The solvent was then distilled off to give 148.7 g of methylsulfonylethyl 4-chloro-2-hydroxyiminoacetoacetate as an oil.

NMR (60 MHz, DMSO-d$_6$) δ: 1.90 (3H, s, SO$_2$C$\underline{H}_3$), 3.52 (2H, t, J=7 Hz, —C$\underline{H}_2$SO$_2$—), 4.58 (2H, t, J=7 Hz, CH$_2$C$\underline{H}_2$SO$_2$), 4.87 (2H, s, ClC$\underline{H}_2$—).

IR (Neat) cm$^{-1}$: 3250, 1750, 1710, 1635.

EXAMPLE 3

In a mixture of 594 ml of ethanol and 60 ml of water was dissolved 148.7 g (0.613 mole) of oily methylsulfonylethyl 4-chloro-2-hydroxyiminoacetoacetate as obtained in Example 2, and 50.0 g (0.656 mole) of thiourea and 74.4 g (0.547 mole) of sodium acetate were directly added. The mixture was stirred at 25°–30° C. for about 30 minutes and 300 ml of ethanol was added. The mixture was cooled to 0° C. or below, and the crystalline precipitate was collected by filtration to give 104.3 g of methylsulfonylethyl 2-(2-aminothiazol-4-yl)-(Z)-2-hydroxyiminoacetate as white crystals. (Yield: 55.2% based on methylsulfonylethyl 4-chloroacetoacetate)

Elemental analysis: Calcd. for C$_8$H$_{11}$N$_3$O$_5$S$_2$=293.31: C32.76%, H3.78%, N14.33%. Found: C32.22%, H3.72%, N13.95%.

NMR (60 MHz, DMSO-d$_6$) δ: 3.00 (3H, s, SO$_2$C$\underline{H}_3$), 3.58 (2H, t, J=7 Hz, —C$\underline{H}_2$SO$_2$), 4.62 (2H, t, J=7 Hz, COC$\underline{H}_2$CH$_2$), 6.90 (1H, s, thiazole 5—H), 7.10 (2H, s, N$\underline{H_2}$—).

IR$\nu_{max}^{KBr}$ cm$^{-1}$: 3450, 3300, 1720, 1610, 1535, 1408, 1290.

EXAMPLE 4

In 200 ml of acetone was suspended 10 g (0.0341 mole) of methylsulfonylethyl 2-(2-aminothiazol-4-yl)-(Z)-2-hydroxyiminoacetate as obtained in Example 3. After a serial addition of 9.98 g (0.0512 mole) of t-butyl bromoacetate, 0.6 ml of water and 18.85 g of anhydrous potassium carbonate, the mixture was stirred at 40° C. for 2 hours followed by addition of 200 ml of water. The mixture was stirred at 30°–35° C. for about an hour, whereby the methylsulfonylethyl group was hydrolytically eliminated. Then, the ethyl acetate was added to the hydrolysis reaction mixture. The organic layer was extracted with water and the aqueous layers were combined and adjusted to pH 2 with 2N HCl. The resulting white crystalline precipitate was collected by filtration and dried to give 9.0 g of 2-(2-aminothiazol-4-yl)-(Z)-2-(t-butoxycarbonylmethoxyimino)acetic acid. (Yiled, 87.6%)

Elemental analysis: Calcd. for C$_{11}$H$_{15}$N$_3$O$_5$S.0.5H$_2$O: C42.58%, H5.20%, N13.54%, S10.33%. Found: C42.62%, H5.23%, N13.74%, S10.87%.

NMR (60 MHz, DMSO-d$_6$) δ: 1.42 (9H, s, C(CH$_3$)$_3$), 4.55 (2H, s, OC$\underline{H}_2$CO) 6.82 (1H, s, thiazole—H), 7.20 (2H, br., NH$_2$).

IR$\nu_{max}^{KBr}$ cm$^{-1}$: 3350, 1745, 1640.

Isolation of the synthesis intermediate, i.e. methylsulfonylethyl 2-(2-aminothiazol-4-yl)-(Z)-2-(t-butoxycarbonylmethoxyimino)acetate, and its physical properties The above-reaction mixture was poured in aqueous hydrochloric acid and extracted with ethyl acetate. The organic layer was washed with water and concentrated to dryness and the concentrate was crystallized from ethyl acetate-isopropyl ether (1:5) to give the desired product.

NMR (60 MHz, DMSO-d$_6$) δ: 1.42 (9H, s, C(CH$_3$)$_3$), 2.99 (3H, s, C$\underline{H}_3$SO$_2$), 3.58 (2H, t, J=7 Hz, —CH$_2$SO$_2$), 4.59 (2H, s, OC$\underline{H}_2$COO), 4.61 (2H, t, J=7 Hz, —OCH$_2$C$\underline{H}_2$SO$_2$), 6.98 (1H, s, thiazole—H), 7.26 (2H, s, NH$_2$—).

IR$\nu_{max}^{KBr}$ cm$^{-1}$: 3410, 1750, 1715, 1623, 1540.

EXAMPLE 5

In 120 ml of acetone was suspended 6 g (0.0205 mole) of methylsulfonylethyl 2-(2-aminothiazol-4-yl)-(Z)-2-hydroxyiminoacetate as obtained in Example 3, followed by a serial addition of 4.6 g (0.0307 mole) of t-butyl chloroacetate, 0.36 ml of water, 11.31 g of anhydrous potassium carbonate and 6.13 g of sodium iodide. The mixture was stirred at 40° C. for 4.5 hours. To this reaction mixture was added 120 ml of water, and the mixture was stirred at 30°–35° C. for an hour. Ethyl acetate was then added as an extraction solvent. The organic layer was separated and extracted with water. The aqueous layers were combined and adjusted to pH 2 with 2N HCl. The resulting white precipitate was collected by filtration and dried to give 4.63 g (yield, 75%) of 2-(2-aminothiazol-4-yl)-(Z)-2-(t-butoxycarbonylmethoxyimino)acetic acid as white crystals.

EXAMPLE 6

(1) In 2.52 liters of methylene chloride was dissolved 840 g of diketene. The solution was cooled to −30° C. or below and 708 g of chlorine gas was bubbled into the solution at −35° to −30° C. for about 2 hours. The solution was stirred for 30 minutes and a solution of 953 g of methylsulfonylethanol and 608 g of pyridine in 1.2 liters of ethylene chloride was added at −20° C. or below over a period of within 30 minutes. The temperature was increased gradually and the reaction was allowed to proceed at −5° C. for about an hour. After completion of the reaction, 8 liters of methylene chloride was added and the mixture was poured into 7 liters of water. After phase separation, the aqueous layer was extracted with methylene chloride. The organic layers were combined, washed with water and concentrated to dryness under reduced pressure to give colorless crystals.

(2) The above-obtained crystals were suspended in a mixture of 1.875 liters of ethyl acetate and 3.75 liters of glacial acetic acid. The suspension was cooled to 5° C. or below and a solution of 530 g of sodium nitrite in 1.665 liters of water was added dropwise at 0°-5° C. over a period of about 2 hours. After completion of addition, the reaction was allowed to proceed for 30 minutes, as the end of which time the reaction mixture was added to 10 liters of ice water to extract. The aqueous layer was separated and further extracted with 5 liters of ethyl acetate. The organic layers were combined, washed with water and concentrated to dryness under reduced pressure to give an oil.

(3) The above-obtained oil was dissolved in a mixture of 8.34 liters of ethanol and 0.43 liter of water, and 530 g of thiourea and 1045 g of sodium acetate were directly added. The reaction was allowed to proceed at room temperature for an hour. The reaction mixture was concentrated under reduced pressure and 8 liter of ethanol was added to the residue. The mixture was then cooled to 5° C. or below and the crystalline precipitate was collected by filtration and dried in vacuo at 40° C. to give 1250 g of methylsulfonylethyl 2-(2-aminothiazol-4-yl)-(Z)-2-hydroxyiminoacetate. (Yield: 55.5% based on methylsulfonylethanol)

NMR (60 MHz, DMSO-d$_6$) δ: 3.02 (3H, s, SO$_2$CH$_3$), 3.58 (2H, t, J=7 Hz, C H$_2$SO$_2$), 4.60 (2H, t, J=7 Hz, OCH$_2$ CH$_2$), 6.90 (1H, s, thiazole 5—H), 7.16 (2H, s, NH$_2$—).

IR (KBr) cm$^{-1}$: 3450, 3300, 1720, 1610, 1535, 1410.

EXAMPLE 7

In 200 ml of acetonitrile was suspended 10 g of methylsulfonylethyl 2-(2-aminothiazol-4-yl)-(Z)-2-hydroxyiminoacetate as obtained in Example 3, and 7.7 g of t-butyl chloroacetate was added. Then, after a serial addition of 1.2 ml of water, 18.85 g of anhydrous potassium carbonate powder and 5.6 g of sodium iodide, the reaction was allowed to proceed at room temperature. After completion of the reaction, the precipitate was filtered off. To the filtrate was added 300 ml of water, and a 40% solution of potassium carbonate was added dropwise for hydrolysis while maintaining pH at 10–10.5. The reaction mixture was then adjusted to pH 2 with 2N hydrochloric acid, whereupon a white precipitate separated out. After cooling to 5° C. or below, the crystalline precipitate was collected by filtration and dried to give 7.09 g of 2-(2-aminothiazol-4-yl)-(Z)-2-(t-butoxycarbonylmethoxyimino)acetate acid as white crystals.

NMR (60 MHz, DMSO-d$_6$) δ: 1.40 (9H, s, C(CH$_3$)$_3$), 4.53 (2H, s, OCH$_2$CO) 6.80 (1H, s, thiazole 5—H), 7.20 (2H, br., NH$_2$).

IR$\nu_{max}^{KBr}$ cm$^{-1}$: 3350, 1745, 1640.

EXAMPLE 8

(1) In 100 ml of acetone was suspended 5 g (0.017 mole) of methylsulfonylethyl 2-(2-aminothiazol-4-yl)-(Z)-2-hydroxyiminoacetate and 5.33 g (0.0255 mole) of t-butyl 2-bromopropionate was added. After a serial addition of 0.3 ml of water and 9.4 g of anhydrous potassium carbonate, the mixture was stirred at 40° C. for about 2.5 hours. After completion of the reaction, the insoluble matter was filtered off. To the filtrate was added 100 ml of water and the mixture was extracted with 150 ml of ethyl acetate. The organic layer was washed with 50 ml of saturated aqueous sodium chloride solution and dried over anhydrous sodium sulfate. The sodium sulfate was filtered off and the filtrate was concentrated to dryness under reduced pressure. The concentrate was crystallized from ethyl acetate-isopropyl ether (1:5, v/v). After cooling to 0° C. or below, the crystalline precipitate was collected by filtration and dried under reduced pressrue to give 5.4 g (yield, 75.4%) of methylsulfonylethyl 2-(2-aminothiazol-4-yl)-(Z)-2-(t-butoxycarbonyl-1-methylmethoxyimino)acetate as white crystals.

Elemental analysis: Calcd. for C$_{15}$H$_{23}$N$_3$O$_7$S$_2$=421.48: C42.75%, H5.50%, N9.97%. Found: C42.98%, H5.31%, N9.71%.

NMR (60 MHz, DMSO-d$_6$) δ: 1.31–1.44 (12H, m, CH$_3$—CH and C(CH$_3$)$_3$), 3.02 (3H, s, SO$_2$CH$_3$), 3.49 (2H, t, J= 7 Hz, CH$_2$SO$_2$), 4.50–4.75 (3H, m, COOCH$_2$ and CH—CH$_3$), 6.96 (1H, s, thiazole 5—H), 7.25 (2H, s, NH$_2$).

IR$\nu_{max}^{KBr}$ cm$^{-1}$: 3400–2995, 1750, 1720, 1630, 1550.

(2) In a mixture of 12 ml of acetone and 6 ml of water was dissolved 0.3 g (0.71 millimole) of methylsulfonylethyl 2-(2-aminothiazol-4-yl)-(Z)-2-t-butoxycarbonyl-1-methylmethoxyimino)acetate as obtained in (1). The solution was warmed to 30°-32° C. and a 40% aqueous solution of potassium carbonate was added dropwise while maintaining the pH at 10–10.5. The reaction mixture was adjusted to pH about 6 with 1N HCl and the solvent was distilled off under reduced pressure. Then, pH was further adjusted to 2 with 1N HCl, whereupon a white crystalline precipitate separated out. After cooling, the precipitate was collected by filtration and dried to give 0.18 g (yield, 80.3%) of 2-(2-aminothiazol-4-yl)-(Z)-2-(t-butoxycarbonyl-1-methylmethoxyimino)acetic acid as white crystals.

NMR (60 MHz, DMSO-d$_6$) δ: 1.30–1.40 (12H, m, CH$_3$—CH and C(CH$_3$)$_3$), 4.55 (1H, q, J=8 Hz, —CHCH$_3$), 6.82 (1H, s, thiazole—5—H).

IR$\nu_{max}^{KBr}$ cm$^{-1}$: 3350, 1725, 1650, 1605, 1455.

Elemental analysis: Calcd. for C$_{12}$H$_{17}$N$_3$O$_5$S.H$_2$O=333.36: C, 43.23%; H, 5.74%, N, 12.61%. Found: C, 43.07%; H, 5.65%; N, 12.36%.

EXAMPLE 9

(1) In 150 ml of methylene chloride was dissolved 39.5 g (0.470 mole) of diketene. The solution was cooled to −30° C. or below and 33.4 g (0.47 mole) of chlorine gas was bubbled into the solution at −35° to −30° C. for about 1.5 hours. The solution was stirred for 30 minutes and a solution of 50 g (0.362 mole) of ethylsulfonylethanol and 28.7 g (0.362 mole) of pyridine in 75 ml of methylene chloride was added dropwise at −20° C. or below over a period of 30 minutes. The temperature was increased and the reaction was allowed to proceed at −5° C. for about 30 minutes. The reaction mixture was poured into water and 400 ml of methylene chloride was added as an extraction solvent. The aqueous layer was further extracted with methylene chloride and the organic layers were combined, washed with water and concentrated to dryness to give 87.0 g of ethylsulfonylethyl 4-chloroacetoacetate. (Yield, 93.6% based on ethylsulfonylethanol)

NMR (60 MHz, CDCl$_3$) δ: 1.40 (3H, t, J=8 Hz, CH$_2$CH$_3$), 3.05 (2H, q, J=8 Hz, SO$_2$CH$_2$CH$_3$), 3.32 (2H, t, J=8 Hz, CH$_2$CH$_2$SO$_2$), 3.71 (2H, s, ClCH$_2$CO—), 4.30 (2H, s, COCH$_2$CO)4. 60 (2H, t, J=8 Hz, COOCH$_2$CH$_2$S).

IR $\nu_{max}^{KBr}$ cm$^{-1}$: 1740, 1730.

(2) In a mixture of 190 ml of glacial acetic acid and 75 ml of ethyl acetate was suspended 87 g (0.339 mole) of ethylsulfonylethyl 4-chloroacetoacetate as obtained in (1). The suspension was cooled to 10° C. or below and a solution of 23.4 g of sodium nitrite in 100 ml of water was added at 0°-5° C. over a period of about an hour. The mixture was stirred for about an hour, added to ice water and extracted with ethyl acetate. The organic layer was washed with water and dried over anhydrous sodium sulfate. The solvent was then distilled off under reduced pressure to give 84.8 g of ethylsulfonylethyl 4-chloro-2-hydroxyiminoacetoacetate as white crystals. (Yield, 87.6%)

NMR (60 MHz, DMSO-d$_6$) δ: 1.20 (3H, t, J=8 Hz, CH$_2$CH$_3$), 3.10 (2H, q, J=8 Hz, SO$_2$CH$_2$CH$_3$), 3.52 (2H, t, J=8 Hz, CH$_2$SO$_2$CH$_2$), 4.60 (2H, t, J=8 Hz, COOCH$_2$CH$_2$), 4.90 (2H, s, C l CH$_2$CO).

IR $\nu_{max}^{KBr}$ cm$^{-1}$: 3450, 1745, 1710, 1635.

(3) In a mixture of 384 ml of ethanol and 38.4 ml of water was dissolved 83.8 g (0.293 mole) of crude ethylsulfonylethyl 4-chloro-2-hydroxyiminoacetoacetate as obtained in (2) and 22.3 g of thiourea and 39.9 g of sodium acetate were added directly to the solution. The mixture was stirred at 25°-30° C. for about an hour and the ethanol was distilled off under reduced pressure, followed by addition 1 liter of water. The mixture was cooled to 5° C. or below and the resulting crystalline precipitate was collected by filtration to give 45.1 g of ethylsulfonylethyl 2-(2-aminothiazol-4-yl)-(Z)-2-hydroxyiminoacetate as white crystals. (Yield, 50.0%)

Elemental analysis: Calcd. for C$_9$H$_{13}$N$_3$O$_5$S$_2$=307.34; C35.17%, H4.26%, N13.67%, S20.86%. Found: C35.24%, H4.23%, N13.52%, S20.68%.

NMR (60 MHz, DMSO-d$_6$) δ: 1.19 (3H, t, J=8 Hz, —CH$_2$CH$_3$), 3.12 (2H, q, J=8 Hz, SO$_2$CH$_2$CH$_3$), 3.52 (2H, t, J=8 Hz, —CH$_2$CH$_2$S), 4.58 (2H, t, J=8 Hz, COOCH$_2$), 6.90 (1H, s, thiazole—5—H), 7.15 (2H, s, NH$_2$—).

IR $\nu_{max}^{KBr}$ cm$^{-1}$: 3400-3100, 1730, 1615, 1535.

EXAMPLE 10

(1) In 180 ml of acetone was suspended 6 g (0.019 mole) of ethylsulfonylethyl 2-(2-aminothiazol-4-yl)-(Z)-2-hydroxyiminoacetate as obtained in Example 9 followed by a serial addition of 5.7 g (0.0292 mole) of t-butyl bromoacetate, 0.9 ml of water and 10.8 g of anhydrous potassium carbonate. The mixture was stirred at 40° C. for 2 hours and the insoluble matter was filtered off. To the filtrate was added 200 ml of water and 200 ml of ethyl acetate was added to extract the reaction product. The aqueous layer was further extracted with ethyl acetate. The organic layers were combined, washed with water and concentrated to dryness under reduced pressure to give 6.0 g of ethylsulfonylethyl 2-(2-aminothiazol-4-yl)-(Z)-2-(t-butoxycarbonylmethoxyimino)acetate as white crystals. (Yield, 73.0%)

NMR (60 MHz, DMSO-d$_6$) δ: 1.20 (3H, t, J=8 Hz, CH$_2$CH$_3$), 1.44 (9H, s, C (CH$_3$)$_3$), 3.12 (2H, q, J=8 Hz, SCH$_2$CH$_3$), 3.55 (2H, t, J=7 Hz, CH$_2$S), 4.52-4.60 (4H, m, COOCH$_2$CO & COO CH$_2$CH$_2$), 7.00 (1H, s, thiazole—5—H), 7.28 (2H, s, NH$_2$—).

IR $\nu_{max}^{KBr}$ cm$^{-1}$: 3400-2950, 1750, 1740, 1715, 1630 1615, 1550.

(2) In 100 ml of acetone-water (1:1, v/v) was dissolved 5.0 g (0.0119 mole) of ethylsulfonylethyl 2-(2-aminothiazol-4-yl)-(Z)-2-(t-butoxycarbonylmethoxyimino)acetate as obtained in (1) and a 40% aqueous solution of potassium carbonate was added dropwise at 30°-35° C. while maintaining the pH at 10-10.5. After completion of the reaction, the solvent was distilled off and pH was adjusted to 2 with 1N-HCl, whereupon white crystals separated out. After cooling, the crystals were collected by filtration to give 2.8 g of 2-(2-aminothiazol-4-yl)-(Z)-2-(t-butoxycarbonylmethoxyimino)acetic acid. (Yield, 78.1%)

The NMR and IR spectra of this product were in good agreement with those of an authentic sample.

EXAMPLE 11

(1) In 100 ml of methylene chloride was dissolved 20.5 g (0.244 mole) of diketene, and 17.3 g (0.244 mole) of chlorine gas was bubbled into the solution with cooling at −30° C. or below. A solution of 35 g (0.188 mole) of phenylsulfonylethanol and 14.9 g (0.188 mole) of pyridine in 75 ml of methylene chloride was added dropwise to the above solution with cooling at −25° C. or below over a period of 30 minutes. The mixture was stirred at 0° C. for about an hour and poured into ice water for separation. The aqueous layer was further extracted with 140 ml of methylene chloride. The organic layers were combined, washed with water and concentrated to dryness to give 54.9 g (yield, 95.8%) of phenylsulfonylethyl 4-chloroacetoacetate as an oil.

NMR (60 MHz, DMSO-d$_6$) δ: 3.49 (4H, m, CH$_2$SO$_2$ and OCH$_2$CO), 4.20 (2H, s, ClCH$_2$CO), 4.49 (2H, t, J=8 Hz, CO OCH$_2$CH$_2$).

IR $\nu_{max}^{Neat}$ cm$^{-1}$: 1755, 1735, 1450, 1400.

(2) In a mixture of 119 ml of acetic acid and 47 ml of ethyl acetate was dissolved 54.3 g (0.178 mole) of oily phenylsulfonylethyl 4-chloroacetoacetate as obtained in (1). The solution was cooled to 5° C. or below and a solution of 12.3 g (0.178 mole) of sodium nitrite in 63 ml of water was added dropwise to the above solution over a period of about an hour. The mixture was stirred for an hour, poured into 300 ml of ice water and extracted with 500 ml of ethyl acetate. The aqueous layer was further extracted with 100 ml of ethyl acetate. The organic layers were combined, washed with 100 ml of 5% aqueous sodium hydrogen carbonate and concentrated to dryness under reduced pressure to give 62.5 g (Yield, 105.2%) of phenylsulfonylethyl 4-chloro-2-hydroxyiminoacetoacetate as an oil. This oil contained a little amount of acetic acid as impurity.

NMR (60 MHz, CDCl$_3$) δ: 3.57 (2H, t, J=8 Hz, —CH$_2$SO$_2$), 4.50 (2H, s, Cl CH$_2$CO), 4.62 (2H, t, J=8 Hz, COOC H$_2$CH$_2$), 7.55-8.00 (5H, m, arom.).

IR $\nu_{max}^{Neat}$ cm$^{-1}$: 3300, 1750, 1710, 1630, 1590, 1450.

(3) In a mixture of 273 ml of ethanol and 27.3 ml of water was dissolved 62.5 g (0.187 mole, unadjusted for purity) of crude phenylsulfonylethyl 4-chloro-2-hydroxyiminoacetoacetate as obtained in (2), and 14.1 g (0.185 mole) of thiourea and 25.1 g (0.184 mole) of sodium acetate were added directly to the solution. The mixture was stirred at 25°–30° C. for about 5 hours and 1 liter of water was added. The mixture was cooled to 5° C. or below and the resulting crystalline precipitate was collected by filtration to give 28.4 g of phenylsulfonylethyl 2-(2-aminothiazol-4-yl)-(Z)-2-hydroxyiminoacetate as white crystals. (Yield: 44.9% based on phenylsulfonylethyl 4-chloroacetoacetate)

Elemental analysis: Calcd. for $C_{13}H_{13}N_3O_5S_2 = 355.38$: C43.94%, H3.69%, N11.82%, S18.04%. Found: C43.90%, H3.73%, N11.40%, S17.37%.

NMR (60 MHz, DMSO-$d_6$) δ: 3.77 (2H, t, J=8 Hz, —CH$_2$S), 4.48 (2H, t, J=8 Hz, COC$\underline{H}_2$CH$_2$), 6.80 (1H, s, thiazole—5—H), 7.20 (2H, s, NH$_2$—), 7.5 0–8.00 (5H, m, arom.).

IR $\nu_{max}^{KBr}$ cm$^{-1}$: 3400–3100, 1725, 1615, 1535.

EXAMPLE 12

(1) In 100 ml of acetone was suspended 5 g (0.0141 mole) of phenylsulfonylethyl 2-(2-aminothiazol-4-yl)-(Z)-2-hydroxyiminoacetate as obtained in Example 11. After a serial addition of 4.0 g (0.0205 mole) of t-butyl bromoacetate, 0.3 ml of water and 7.7 g of anhydrous potassium carbonate, the mixture was stirred at 40° C. for 1.5 hours. After completion of the reaction, the insoluble matter was filtered off and 100 ml of water and 100 ml of ethyl acetate were added to extract the reaction product. The aqueous layer was further extracted with ethyl acetate and the organic layers were combined, washed twice with saturated aqueous sodium chloride and dried over anhydrous sodium sulfate. The solvent was then distilled off under reduced pressure and ethyl acetate-isopropyl ether (1:5, v/v) was added to the residue, whereupon white crystals separated out. After cooling, the crystals were collected by filtration to give 4.1 g (yield, 62%) of phenylsulfonylethyl 2-(2-aminothiazol-4-yl)-(Z)-2-(t-butoxycarbonylmethoxyimino)acetate.

NMR (60 MHz, DMSO-$d_6$) δ: 1.40 (9H, s, C (C$\underline{H}_3$)$_3$), 3.76 (2H, t, J=8 Hz, C$\underline{H}_2$SO$_2$), 4.40–4.60 (4H, m, COOC$\underline{H}_2$CH$_2$ and OC$\underline{H}_2$COO), 6.86 (1H, s, thiazole—5—H), 7.25 (2H, s, NH$_2$) 7.50–8.00 (5H, m, arom.).

IR $\nu_{max}^{KBr}$ cm$^{-1}$: 3400–2900, 1750, 1710, 1620, 1550.

(2) In 20 ml of acetone-water (1:1, v/v) was dissolved 1 g (0.00213 mole) of phenylsulfonylethyl 2-(2-aminothiazol-4-yl)-(Z)-2-(t-butoxycarbonylmethoxyimino)acetate as obtained in (1), and a 40% aqueous solution of potassium carbonate was added dropwise to the solution while maintaining the pH at 10–10.5. After completion of the reaction, the mixture was adjusted to pH 6 with 1N HCl and the acetone was distilled off. Then, pH was adjusted to 2 with 1N HCl, whereupon white crystals separated out. After cooling, the crystals were collected by filtration to give 0.42 g (yield, 65.4%) of 2-(2-aminothiazol-4-yl)-(Z)-2-(t-butoxycarbonylmethoxyimino)acetic acid.

NMR (60 MHz, DMSO-$d_6$) δ: 1.42 (9H, s, C (C$\underline{H}_3$)$_3$), 4.56 (2H, s, OC$\underline{H}_2$CO) 6.85 (1H, s, thiazole —5—$\underline{H}$), 7.25 (2H, br, N$\underline{H}_2$—).

IR $\nu_{max}^{KBr}$ cm$^{-1}$: 3550–2900, 1745, 1645, 1610, 1580.

EXAMPLE 13

Using 2 g (0.00563 mole) of phenylsulfonylethyl 2-(2-aminothiazol-4-yl)-(Z)-2-hydroxyiminoacetate as obtained in Example 11 and 1.17 g (0.00559 mole) of t-butyl 2-bromopropionate and following the reaction procedure of Example 12, there was obtained 1.63 g (yield, 60.0%) of phenylsulfonylethyl 2-(2-aminothiazol-4-yl)-(Z)-2-(t-butoxycarbonyl-1-methylmethoxyimino)acetate.

NMR (60 MHz, DMSO-$d_6$) δ: 1.38–1.42 (12H, m, C (CH$_3$)$_3$ and CH—C$\underline{H}_3$), 3.73 (2H, t, J=7 Hz, CH$_2$SO$_2$), 4.45–4.60 (3H, m, COOC$\underline{H}_2$ and C$\underline{H}$CH$_3$) 6.90 (1H, s, thiazole—5—H), 7.20 (2H, s, N$\underline{H}_2$), 7.48–8.00 (5H, m, arom.).

IR $\nu_{max}^{KBr}$ cm$^{-1}$: 3400–2950, 1745, 1730, 1630, 1595, 1550.

The above-obtained phenylsulfonylethyl 2-(2-aminothiazol-4-yl)-(Z)-2-(t-butoxycarbonyl-1-methylmethoxyimino)acetate (1.2 g, 0.00248 mole) was hydrolyzed to give 0.52 g (yield, 66.5%) of 2-(2-aminothiazol-4-yl)-(Z)-2-(t-butoxycarbonyl-1-methylmethoxyimino)acetic acid.

The NMR and IR of this product were in good agreement with those of the product obtained in Example 8.

EXAMPLE 14

Using 5 g (0.0141 mole) of phenylsulfonylethyl 2-(2-aminothiazol-4-yl)-(Z)-2-hydroxyiminoacetate as obtained in Example 11 and 4.7 g (0.0211 mole) of t-butyl 2-bromoisobutyrate and following the reaction procedure of Example 12, there was obtained 4.1 g (yield, 58.4%) of phenylsulfonylethyl 2-(2-aminothiazol-4-yl)-(Z)-2-(t-butoxycarbonyl-1,1-dimethylmethoxyimino)acetate.

NMR (60 MHz, DMSO-$d_6$) δ: 1.40 (15H, s, C (CH$_3$)$_3$ and C (CH$_3$)$_2$), 3.72 (2H, t, J=8 Hz, C$\underline{H}_2$SO$_2$), 4.60 (2H, t, J=8 Hz, COOC$\underline{H}_2$), 6.90 (1H, s, thiazole—5—H), 7.27 (2H, s, NH$_2$), 7.49–7.98 (5H, m, arom.).

IR $\nu_{max}^{KBr}$ cm$^{-1}$: 3400–3000, 1750, 1715, 1635, 1595, 1545.

Then, the above ester compound was hydrolyzed to give 2-(2-aminothiazol-4-yl)-(Z)-2-(t-butoxycarbonyl-1,1-dimethylmethoxyimino)acetic acid. (Yield, 72.0%)

Elemental analysis: Calcd. for $C_{13}H_{19}N_3O_5S.0.7H_2O = 341.98$: C45.67%, H6.01%, N12.29%. Found: C45.99%, H6.32%, N12.32%.

NMR (60 MHz, DMSO-$d_6$) δ: 1.41 (15H, s, C (CH$_3$)$_2$ and C (CH$_3$)$_3$), 6.79 (s, 1H, thiazole—5—H), 7.20 (2H, br. —N$\underline{H}_2$).

IR $\nu_{max}^{KBr}$ cm$^{-1}$: 3400–2900, 1720, 1645, 1600.

EXAMPLE 15

(1) In 1.26 liters of methylene chloride was dissolved 420 g (5.0 moles) of diketene. The solution was cooled at −30° to −35° C. and 354 g (4.99 moles) of chlorine gas was bubbled into the solution for about an hour to prepare a 4-chloroacetoacetyl chloride solution. 244 ml of this solution (4-chloroacetoacetyl chloride: 109.2 g, 0.705 mole) was cooled to −30° to −40° C. and a solution of 50 g (0.543 mole) of methylthioethanol and 43 g (0.543 mole) of pyridine in 85 ml of methylene chloride was added dropwise at −20° to −30° C. over a period of about 30 minutes. After completion of addition, the reaction was allowed to proceed at −5° C. for 30 minutes. To the reaction mixture were added 500 ml of methylene chloride and 1 liter of water to extract the reaction product. The aqueous layer was further extracted with 500 ml of methylene chloride. The organic layers were combined, washed with 500 ml of water and concentrated to dryness under reduced pressure to give 114 g of methylthioethyl 4-chloroacetoacetate as an oil.

NMR (60 MHz, DMSO-$d_6$) δ: 2.10 (3H, s, S—C$\underline{H}_3$), 2.71 (2H, t, J=8 Hz, C$\underline{H}_2$S—CH$_3$), 3.72 (2H, s, COC$\underline{H}$-

₂CO) 4.25 (2H, t, J=8 Hz, COOCH₂CH₂), 4.60 (2H, s, ClCH₂CO).

IR $\nu_{max}^{Neat}$ cm⁻¹: 1750–1730, 1670.

(2) In a mixture of 115 ml of ethyl acetate and 230 ml of glacial acetic acid was dissolved 114 g (0.541 mole) of crude methylthioethyl 4-chloroacetoacetate as obtained in (1). The solution was cooled to 5° C. or below and a solution of 37.5 g (0.543 mole) of sodium nitrite in 118 ml of water was added dropwise to the solution at 5° C. or below over a period of about 2 hours. The reaction mixture was poured into 1 liter of ice water to extract the reaction product. The aqueous layer was further extracted with 1 liter of ethyl acetate. The organic layers were combined, washed with 400 ml of 5% aqueous sodium hydrogen carbonate and concentrated under reduced pressure to give 130 g of methylthioethyl 4-chloro-2-hydroxyiminoacetoacetate as an oil.

NMR (60 MHz, DMSO-d₆) δ: 2.12 (3H, s, S—CH₃), 2.75 (2H, t, J=8 Hz, CH₂CH₂S), 4.40 (2H, t, J=8 Hz, COOC H₂CH₂), 4.89 (2H, s, ClCH₂CO).

IR $\nu_{max}^{Neat}$ cm⁻¹: 3150–3000, 1745, 1715.

(3) In a mixture of 520 ml of ethanol and 28 ml of water was dissolved 130 g (0.542 mole) of methylthioethyl 4-chloro-2-hydroxyiminoacetoacetate as obtained in (2), and 41.3 g (0.543 mole) of thiourea and 73.9 g (0.543 mole) of sodium acetate were added. The reaction was allowed to proceed at room temperature for 60 minutes. The solvent was then distilled off under reduced pressure, followed by addition of 300 ml of water. The mixture was cooled and the crystalline precipitate was collected by filtration and dried under reduced pressure to give 72.6 g (yield: 51.2% based on methylthioethanol) of methylthioethyl 2-(2-aminothiazol-4-yl)-(Z)-2-hydroxyiminoacetate as white crystals.

Elemental analysis: Calcd. for C₈H₁₁N₃O₃S₂=261.31: C36.77%, H4.24%, N16.08%. Found: C36.71%, H4.23%, N15.94%.

NMR (60 MHz, DMSO-d₆) δ: 2.11 (3H, s, S—CH₃), 2.77 (2H, t, J=8 Hz, CH₂S), 4.38 (2H, t, J=8 Hz, CH₂CH₂S), 6.84 (1H, s, thiazole—5—H), 7.15(2H, s, NH₂).

IR $\nu_{max}^{KBr}$ cm⁻¹: 3400–3150, 1720, 1610, 1535.

EXAMPLE 16

(1) In 100 ml of acetone was suspended 5 g (0.0191 mole) of methylthioethyl 2-(2-aminothiazol-4-yl)-(Z)-2-hydroxyiminoacetate as obtained in Example 15, and 4.32 g (0.029 mole) of t-butyl chloroacetate, 0.3 ml of water, 10.56 g (0.076 mole) of anhydrous potassium carbonate and 3.15 g (0.021 mole) of sodium iodide were added in that order. The reaction was allowed to proceed at 40° C. for about 6 hours. The reaction mixture was poured into 300 ml of water and extracted with 500 ml of ethyl acetate. The organic layer was washed with water, dehydrated with anhydrous sodium sulfate and concentrated to dryness under reduced pressure. Ether was added to the residue to give 6.56 g (yield, 91.5%) of methylthioethyl 2-(2-aminothiazol-4-yl)-(Z)-2-(t-butoxycarbonylmethoxyimino)acetate as white crystals.

Elemental analysis: Calcd. for C₁₄H₂₁N₃O₃S₂=375.46: C44.79%, H5.64%, N11.19%. Found: C45.07%, H5.78%, N11.05%.

NMR (60 MHz, DMSO-d₆) δ: 1.42 (9H, s, CH₃×3), 2.10 (3H, s, SCH₃), 2.78 (2H, t, J=8 Hz, CH₂SCH₃), 4.40 (2H, t, J=8 Hz, COOCH₂CH₂S), 4.57 (2H, s, OCH₂CO), 6.92 (1H, s, thiazole—5—H), 7.25 (2H, s, NH₂—).

IR $\nu_{max}^{KBr}$ cm⁻¹: 3400–2900, 1740, 1710, 1626, 1550.

(2) In a mixture of 47 ml of acetone and 9.4 ml of water was dissolved 6.0 g (0.0160 mole) of methylthioethyl 2-(2-aminothiazol-4-yl)-(Z)-2-(t-butoxycarbonylmethoxyimino)acetate as obtained in (1), and 0.05 g of ammonium molybdate was added. Further, 10.9 ml (0.112 mole) of 35% aqueous hydrogen peroxide was added at 25°–30° C. and the reaction was allowed to proceed for 6 hours. The reaction mixture was poured into 500 ml of water and extracted with 500 ml of ethyl acetate. The organic layer was washed with 500 ml of 5% sodium sulfite and 500 ml of water and concentrated to dryness. To the residue was added about 50 ml of ether, whereby white crystals separated out. After cooling, the crystals were collected by filtration to give 6.1 g (Yield, 93.6%) of methylsulfonylethyl 2-(2-aminothiazol-4-yl)-(Z)-2-(t-butoxycarbonylmethoxyimino)acetate.

Elemental analysis: Calcd. for C₁₄H₂₁N₃O₇S₂.0.5-H₂O=416.47; C40.38%, H5.32%, N10.09%. Found: C40.11%, H5.15%, N9.89%.

NMR (60 MHz, DMSO-d₆) δ: 1.42 (9H, s, CH₃×3), 3.00 (3H, s, SCH₃), 3.57 (2H, t, J=8 Hz, CH₂SCH₃), 4.55–4.62 (4H, m, COOCH₂CH₂ & OCH₂COO), 7.00 (1H, S, thiazole—5—H), 7.28 (2H, s, NH₂—).

IR $\nu_{max}^{KBr}$ cm⁻¹: 3400–2995, 1750, 1720, 1628, 1545.

(3) In a mixture of 200 ml of acetone and 200 ml of water was dissolved 4 g (0.00982 mole) of methylsulfonylethyl 2-(2-aminothiazol-4-yl)-(Z)-2-(t-butoxycarbonylmethoxyimino)acetate as obtained in (2), and a 40% aqueous solution of potassium carbonate was added dropwise to the solution at 30°–35° C. while maintaining pH at about 10.5. The reaction mixture was washed with 500 ml of ethyl acetate. The aqueous layer was adjusted to pH about 2 with 2N HCl, whereby crystals separated out. After cooling the crystalline precipitate was collected by filtration to give 2.5 g (yield, 84.5%) of 2-(2-aminothiazol-4-yl)-(Z)-2-(t-butoxycarbonylmethoxyimino)acetic acid as white crystals.

Elemental analysis: Calcd. for C₁₁H₁₅N₃O₅S.0.5-H₂O=310.32: C42.58%, H5.20%, N13.54%. Found: C42.95%, H5.12%, N13.38%.

NMR (60 MHz, DMSO-d₆) δ: 1.44 (9H, s, CH₃×3), 4.57 (2H, s, OCH₂CO), 6.85 (1H, s, thiazole—5—H), 7.25 (2H, br, NH₂).

IR $\nu_{max}^{KBr}$ cm⁻¹: 3350–3000, 1740, 1640, 1600, 1580.

EXAMPLE 17

(1) In 100 ml of acetone was suspended 5 g (0.0191 mole) of methylthioethyl 2-(2-aminothiazol-4-yl)-(Z)-2-hydroxyiminoacetate as obtained in Example 15, and 6.4 g (0.0287 mole) of t-butyl 2-bromoisobutyrate, 0.3 ml of water and 10.56 g (0.076 mole) of anhydrous potassium carbonate were added in that order. The reaction was allowed to proceed at 40° C. for 20 hours. The reaction mixture was poured into 100 ml of water and extracted with 100 ml of ethyl acetate. The organic layer was washed with water and dried over anhyrous sodium sulfate and concentrated to dryness. To the residue was added 50 ml of ether and the mixture was cooled. The precipitate was collected by filtration to give 6.17 g (yield, 80.0%) of methylthioethyl 2-(2-aminothiazol-4-yl)-(Z)-2-(t-butoxycarbonyl-1,1-dimethylmethoxyimino)acetate as white crystals.

Elemental analysis: Calcd. for C₁₆H₂₅N₃O₅S₂=403.51: C47.63%, H6.24%, N10.41%. Found: C47.37%, H6.23%, N10.34%.

NMR (60 MHz, DMSO-d$_6$) δ: 1.40 (15H, S, C(CH$_3$)$_3$ and C(CH$_3$)$_2$), 2.12 (3H, s, —SCH$_3$), 2.78 (2H, t, J=8 Hz, CH$_2$SCH$_3$), 4.41 (2H, t, J=8 Hz, —CH$_2$CH$_2$S), 6.88 (1H, s, thiazole—5—H), 7.26 (2H, s, NH$_2$—).

IR $\nu_{max}^{KBr}$ cm$^{-1}$: 3400–3000, 1735, 1730, 1630, 1550.

(2) In a mixture of 25 ml of acetone and 5 ml of water was dissolved 2.5 g (0.0062 mole) of methylthioethyl 2-(2-aminothiazol-4-yl)-(Z)-2-(t-butoxycarbonyl-1,1-dimethylmethoxyimino)acetate as obtained in (1), and 0.029 g of ammonium molybdate was added. Then, at 30° C., 1.94 ml of 35% aqueous hydrogen peroxide was added dropwise to the mixture. The resulting mixture was stirred at the same temperature for 7.5 hours, poured into 200 ml of water and extracted with 200 ml of ethyl acetate. The organic layer was washed with 400 ml of 5% sodium sulfite and 200 ml of water and the solvent was distilled off under reduced pressure. To the residue was added 100 ml of ether, whereupon white crystals separated out. After cooling, the crystals were collected by filtration to give 2.4 g (yield, 88.9%) of methylsulfonylethyl 2-(2-aminothiazol-4-yl)-(Z)-2-(t-butoxycarbonyl-1,1-dimethylmethoxyimino)acetate.

Elemental analysis: Calcd. for C$_{16}$H$_{25}$N$_3$O$_7$S$_2$=435.51: C44.13%, H5.79%, N9.65%. Found: C44.15%, H5.83%, N9.60%.

NMR (60 MHz, DMSO-d$_6$) δ: 1.40 (15H, S, CH$_3$×5), 3.04 (3H, a, SCH$_3$), 3.58 (2H, t, J=8 Hz, CH$_2$SCH$_3$), 4.62 (2H, t, J=8 Hz, CH$_2$CH$_2$SCH$_3$), 6.92 (1H, s, thiazole—5—H), 7.28 (2H, br, NH$_2$—).

IR $\nu_{max}^{KBr}$ cm$^{-1}$: 3350–3000, 1750, 1725, 1645, 1550.

(3) In a mixture of 45 ml of acetone and 45 ml of water was dissolved 2.2 g (0.00505 mole) of methylsulfonylethyl 2-(2-aminothiazol-4-yl)-(Z)-2-(t-butoxycarbonyl-1,1-dimethylmethoxyimino)acetate as obtained in (2), and a 40% aqueous solution of potassium carbonate was added dropwise to the solution at 30°–35° C. while maintaining the pH at 10–10.5. The mixture was stirred for about an hour and washed with 100 ml of ethyl acetate. The aqueous layer was adjusted to pH about 2 with 2N HCl and then cooled. The white crystals were collected by filtration to give 1.29 g (yield, 77.6%) of 2-(2-aminothiazol-4-yl)-(Z)-2-(t-butoxycarbonyl-1,1-dimethylmethoxyimino)acetic acid.

Elemental analysis: Calcd. for C$_{13}$H$_{19}$N$_3$O$_5$S.0.77-H$_2$O=343.23: C45.49%, H6.02%, N12.24%, S9.34%. Found: C45.49%, H6.22%, N12.17%, S9.24%.

NMR (60 MHz, DMSO-d$_6$) δ: 1.40 (15H, S, (CH$_3$)$_3$ and C(CH$_3$)$_2$), 6.79 (1H, s, thiazol—5—H), 7.20 (2H, br, NH$_2$—).

IR $\nu_{max}^{KBr}$ cm$^{-1}$: 3550–2800, 1720, 1650, 1630, 1610, 1580, 1560.

EXAMPLE 18

Using 146 g (0.942 mole) of 4-chloroacetoacetyl chloride (synthesized from diketene and chlorine) and 100 g (0.942 mole) of ethylthioethanol and following the procedure of Example 15, there was obtained 138.8 g of ethylthioethyl 2-(2-aminothiazol-4-yl)-(Z)-2-hydroxyiminoacetate via ethylthioethyl 4-chloroacetoacetate and ethylthioethyl 4-chloro-2-hydroxyiminoacetate. (Yield, 53.5% based on ethylthioethanol)

Elemental analysis: Calcd. for C$_9$H$_{13}$N$_3$O$_3$S$_2$=275.34: C39.26%, H4.76%, N15.26%, S23.29%. Found: C39.43%, H4.81%, N15.01%, S23.07%.

NMR (60 MHz, DMSO-d$_6$) δ: 1.28 (3H, t, J=8 Hz, CH$_2$CH$_3$), 2.55 (2H, q, J=8 Hz, CH$_2$SCH$_2$), 2.80 (2H, t, J=8 Hz, CH$_2$CH$_2$S), 4.38 (2H, t, J=8 Hz, COOCH$_2$CH$_2$), 6.86 (1H, s, thiazole—5—H), 7.18 (2H, s, NH$_2$—).

IR $\nu_{max}^{KBr}$ cm$^{-1}$: 3400–3100, 1730, 1620, 1536.

PHYSICAL CHARACTERISTICS OF THE INTERMEDIATES

Ethylthioethyl 4-chloroacetoacetate

NMR (60 MHz, CDCl$_3$) δ: 1.25 (3H, t, J=8 Hz, CH$_2$CH$_3$), 2.55 (2H, q, J=8 Hz, SCH$_2$CH$_3$), 2.77 (2H, t, J=8 Hz, CH$_2$CH$_2$S), 3.68 (2H, s, COOCH$_2$CO), 4.30 (4H, m, COOCH$_2$ and ClCH$_2$CO).

IR $\nu_{max}^{Neat}$ cm$^{-1}$: 1750, 1730, 1670.

Ethylthioethyl 4-chloro-2-hydroxyiminoacetate

NMR (60 MHz, CDCl$_3$) δ: 1.27 (3H, t, J=8 Hz, CH$_2$CH$_3$), 2.60 (2H, q, J=8 Hz, CH$_2$SCH$_2$CH$_3$), 2.82 (2H, t, J=8 Hz, CH$_2$SCH$_2$), 4.45 (2H, t, J=8 Hz, COOCH$_2$), 4.62 (2H, s, ClCH$_2$).

IR $\nu_{max}^{Neat}$ cm$^{-1}$: 3350–2900, 1740, 1710, 1620.

EXAMPLE 19

(1) In 300 ml of acetone was suspended 15 g (0.0545 mole) of ethylthioethyl 2-(2-aminothiazol-4-yl)-(Z)-2-hydroxyiminoacetate as obtained in Example 18, and 12.3 g (0.0187 mole) of t-butyl chloroacetate, 0.9 ml of water, 30.1 g (0.218 mole) of anhydrous potassium carbonate and 8.98 g (0.0599 mole) of sodium iodide were added to the suspension. The reaction was allowed to proceed at room temperature for 10 hours. The precipitate was filtered off and 450 ml of ethyl acetate and 450 ml of water were added for effecting extraction. The aqueous layer was further extracted with 100 ml of ethyl acetate. The organic layers were combined, washed twice with 5% aqueous sodium chloride and dried over anhydrous sodium sulfate. The solvent was then distilled off under reduced pressure and 600 ml of acetone was added to the residue for dissolution, followed by addtion of 1.5 liters of water. The mixture was cooled to 5° C. or below and the resulting crystalline precipitate was collected by filtration to give 19.1 g (yield, 90.0%) of ethylthioethyl 2-(2-aminothiazol-4-yl)-(Z)-2-(t-butoxycarbonylmethoxyimino)acetate.

Elemental analysis: Calcd. for C$_{15}$H$_{23}$N$_3$O$_5$S$_2$=289.48: C, 46.26%; H, 5.95%, N, 10.79%; S, 16.46%. Found: C, 46.56%; H, 6.00%; N, 10.52%; S, 15.88%.

NMR (60 MHz, DMSO-d$_6$) δ: 1.18 (3H, t, J=8 Hz, CH$_2$CH$_3$), 1.44 (9H, s, C(CH$_3$)$_3$), 2.55 (2H, q, J=8 Hz, SCH$_2$CH$_3$), 2.80 (2H, t, J=8 Hz, CH$_2$SCH$_2$), 4.38 (2H, t, J=8 Hz, COOCH$_2$CH$_2$), 4.56 (2H, s, OCH$_2$CO) 6.90 (1H, s, thiazole—5—H), 7.22 (2H, s, NH$_2$—).

IR $\nu_{max}^{KBr}$ cm$^{-1}$: 3450–2900, 1760, 1750, 1620, 1555.

(2) In a mixture of 200 ml of acetone and 40 ml of water was dissolved 19.1 g (0.0490 mole) of ethylthioethyl 2-(2-aminothiazol-4-yl)-(Z)-2-(t-butoxycarbonylmethoxyimino)acetate as obtained in (1). To the solution was added 0.23 g of ammonium molybdate and 8.3 g (0.073 mole) of 30% aqueous hydrogen peroxide was added dropwise with cooling at 30° C. or below. The mixture was stirred for an hour to give an intermediate. Further, 4.73 g (0.417 mole) of 30% aqueous hydrogen peroxide was added dropwise. The mixture was stirred at room temperature overnight and adjusted to pH about 7 with a 40% potassium carbonate solution, and 200 ml of ethyl acetate and 160 ml of water were added for extraction. The aqueous layer was further extracted with 100 ml of ethyl acetate. The organic layers were combined and 5% aqueous sodium sulfite was added with cooling, followed by shaking. The organic solution was then washed with 5% aqueous sodium chloride and dried over anhydrous sodium sulfate. The solvent was then distilled off under reduced pressure and 100 ml of ethyl acetate-isopropyl ether (1:5 v/v) was added to the residue. The mixture was cooled to 5° C. or below and the resulting crystalline precipitate was collected by filtration to give 20.0 g (yield, 96.8%) of ethylsulfonylethyl 2-(2-aminothiazol-4-yl)-(Z)-2-(t-butoxycarbonylmethoxyimino)acetate.

Elemental analysis: Calcd. for $C_{15}H_{23}N_3O_7S_2=421.48$: C42.75%, H5.50%, N9.97%, S15.21%. Found: C42.96%, H5.86%, N9.85%, S14.60%.

NMR (60 MHz, DMSO-$d_6$) δ: 1.20 (3H, t, J=8 Hz, CH$_2$C$\underline{H}_3$), 1.45 (9H, s, C(CH$_3$)$_3$), 3.14 (2H, q, J=8 Hz, SC$\underline{H}_2$CH$_3$), 3.55 (2H, t, J=8 Hz, C$\underline{H}_2$SCH$_2$), 4.60 (4H, m, COOC$\underline{H}_2$ and OC$\underline{H}_2$CO), 7.00 (1H, s, thiazole—5—H) 7.28 (2H, s, NH$_2$—).

IR $\nu_{max}^{KBr}$ cm$^{-1}$: 3400–3000, 1755, 1740, 1715, 1630, 1610, 1545.

The filtrate obtained in the above procedure (2) was poured into water and extracted with ethyl acetate. The extract was concentrated to dryness and the residue was crystallized from ethyl acetate-isopropyl ether (1:1, v/v) to give ethylsulfinylethyl 2-(2-aminothiazol-4-yl)-(Z)-2-(t-butoxycarbonylmethoxyimino)acetate.

Elemental analysis: Calcd. for $C_{15}H_{23}N_3O_6S_2=405.48$: C44.43%, H5.72%, N10.36%, S15.81%. Found: C44.50%, H5.68%, N10.17%, S15.52%.

NMR (60 MHz, DMSO-$d_6$) δ: 1.18 (3H, t, J=8 Hz, CH$_2$C$\underline{H}_3$), 1.42 (9H, s, C(CH$_3$)$_3$), 2.70–3.20, (4H, m, C$\underline{H}_2$SOC$\underline{H}_2$ and C$\underline{H}_2$SOCH$_2$), 4.60 (4H, m, OC$\underline{H}_2$CO and COOC$\underline{H}_2$CH$_2$), 7.00 (1H, s, thiazole—5—H), 7.30 (2H, s, NH$_2$—).

IR $\nu_{max}^{KBr}$ cm$^{-1}$: 3350–2950, 1745, 1720, 1620, 1550.

(3) In 600 ml of acetone-water (1:1, v/v) was dissolved 20 g (0.0475 mole) of ethylsulfonylethyl 2-(2-aminothiazol-4-yl)-(Z)-2-(t-butoxycarbonylmethoxyimino)acetate as obtained in (2), and a 40% aqueous solution of potassium carbonate was added with warming at 30°–35° C. while maintaining the pH at 10–10.5. The mixture was stirred for about an hour and adjusted to pH about 6 with 2N HCl and 300 ml of ethyl acetate was added, followed by shaking. The organic layer was extracted with 30 ml of 5% aqueous sodium chlrodie. The aqueous layers were combined, adjusted to pH 2 with 2N HCl and cooled. The resulting crystalline precipitate was collected by filtration to give 12.5 g (yield, 87.3%) of 2-(2-aminothiazol-4-yl)-(Z)-2-(t-butoxycarbonylmethoxyimino)acetate as white crystals. The NMR and IR of this product were in good agreement with those obtained in (3) of Example 16.

EXAMPLE 20

(1) Using 6 g (0.0218 mole) of ethylthioethyl 2-(2-aminothiazol-4-yl)-(Z)-2-hydroxyiminoacetate as obtained in Example 18 and 6.83 g (0.0327 mole) of t-butyl 2-bromopropionate and followed the procedure (1) of Example 19, there was obtained 7.04 g (yield, 80.0%) of ethylthioethyl 2-(2-aminothiazol-4-yl)-(Z)-2-(t-butoxycarbonyl-1-methylmethoxyimino)acetate.

Elemental analysis: Calcd. for $C_{16}H_{25}N_3O_5S_2=403.51$: C, 47.63%; H, 6.24%; N, 10.40%; S, 15.80%. Found: C, 47.62%; H, 6.15%; N, 10.39%; S, 15.50%.

NMR (60 MHz, DMSO-$d_6$) δ: 1.05–1.40 (15H, m, CH$_2$C$\underline{H}_3$ and CH—C$\underline{H}_3$ and C(CH$_3$)$_3$), 2.55 (2H, q, J=8 Hz, SC$\underline{H}_2$CH$_3$), 2.80 (2H, t, J=8 Hz, —C$\underline{H}_2$SCH$_2$CH$_3$), 4.39 (2H, t, J=8 Hz, COOCH$_2$), 4.48 (1H, q, J=8 Hz, C$\underline{H}$CH$_3$), 6.90 (1H, s, thiazole—5—H), 7.25 (2H, s, N$\underline{H}_2$—).

IR $_{max}^{KBR}$ cm$^{-1}$: 3400–2900, 1730, 1620, 1540.

(2) In 60 ml of acetone-water (5:1, v/v) was dissolved 5 g (0.0124 mole) of ethylthioethyl 2-(2-aminothiazol-4-yl)-(Z)-2-(t-butoxycarbonyl-1-methylmethoxyimino)acetate as obtained in (1) followed by oxidation in the same manner as (2) of Example 19 to give 4.8 g (yield, 88.8%) of ethylsulfonylethyl 2-(2-aminothiazol-4-yl)-(Z)-2-(t-butoxycarbonyl-1-methylmethoxyimino)acetate as white crystals. The acetate was then hydrolyzed in the same manner as (3) of Example 19 to give 2.8 g (yield, 80.6%) of 2-(2-aminothiazol-4-yl)-(Z)-2-(t-butoxycarbonyl-1-methylmethoxyimino)acetic acid.

Elemental analysis: Calcd. for $C_{12}H_{17}N_3O_5S.0.2H_2O=318.94$: C45.19%, H5.50%, N13.17%, S10.05%. Found: C45.40%, H5.95%, N13.07%, S10.35%.

NMR (60 MHZ, DMSO-$d_6$) δ: 1.35 (3H, d, J=8 Hz, CH—C$\underline{H}_3$), 1.44 (9H, s, C (CH$_3$)$_3$), 4.58 (1H, q, J=8 Hz, C$\underline{H}$—CH$_3$), 6.83 (1H, s, thiazole—5—H) 7.25 (2H, br, NH$_2$—).

IR $\nu_{max}^{KBr}$ cm$^{-1}$: 3350–2900, 1725, 1650, 1610, 1590.

EXAMPLE 21

(1) Using 6 g (0.0218 mole) of ethylthioethyl 2-(2-aminothiazol-4-yl)-(Z)-2-hydroxyiminoacetate as obtained in Example 18 and 7.29 g (0.0327 mole) of t-butyl 2-bromoisobutyrate and following the procedure of (1) of Example 19, there was obtained 7.7 g (yield, 84.6%) of ethylthioethyl 2-(2-aminothiazol-4-yl)-(Z)-2-(t-butoxycarbonyl-1,1-dimethylmethoxyimino)acetate.

Elemental analysis: Calcd. for $C_{17}H_{27}N_3O_5S_2=417.54$: C48.90%, H6.52%, N10.06%, S15.36%. Found: C48.96%, H6.45%, N10.29%, S15.33%.

NMR (60 MHz, DMSO-$d_6$) δ: 1.18 (3H, t, J=8 Hz, CH$_2$C$\underline{H}_3$), 1.40 (15H, s, C (CH$_3$)$_3$ and C (CH$_3$)$_2$), 2.55 (2H, q, J=8 Hz, SC$\underline{H}_2$CH$_3$), 2.79 (2H, t, J=8 Hz, —CH$_2$S), 4.38 (2H, t, J=8 Hz, COOC$\underline{H}_2$—), 6.85 (1H, s, thiazole—5—H), 7.25 (2H, s, NH$_2$—).

IR $\nu_{max}^{KBr}$ cm$^{-1}$: 3400–3000, 1740, 1730, 1635, 1550.

(2) Ethylthioethyl 2-(2-aminothiazol-4-yl)-(Z)-2-(t-butoxycarbonyl-1,1-dimethylmethoxyimino)acetate (2 g, 0.0048 mole) as obtained in (1) was oxidized and hydrolyzed in the same manner as (2) and (3) of Example 19 to give 1.1 g (yield, 69.6%) of 2-(2-aminothiazol-4-yl)-(Z)-2-(t-butoxycarbonyl-1,1-dimethylmethoxyimino)acetic acid.

NMR (60 MHz, DMSO-$d_6$) δ: 1.42 (15H, s, C (CH$_3$)$_3$ and C (CH$_3$)$_2$), 6.78 (1H, S, thiazole—5—H), 7.20 (2H, br, NH$_2$—).

IR $\nu_{max}^{KBr}$ cm$^{-1}$: 3400–2900, 1720, 1645, 1600, 1590.

EXAMPLE 22

In 100 ml of methylene chloride was dissolved 35.4 g (0.421 mole) of diketene. The solution was cooled to −30° to −35° C. and 29.5 g (0.415 mole) of chlorine was bubbled into the solution for about an hour to prepare 4-chloroacetoacetyl chloride. The solution was cooled to 40° C. or below and a solution of 50 g (0.324 mole) of phenylthioethanol and 25.6 g (0.324 mole) of pyridine in 52 ml of methylene chloride was added dropwise to the solution at −20° C. or below over a period of about an hour. After completion of addition, the reaction was allowed to proceed at −5° C. for about an hour. To the reaction mixture were added 400 ml of methylene chloride and 700 ml of water to extract the reaction product. The aqueous layer was further extracted with 200 ml of methylene chloride. The organic layers were combined, washed with water and concentrated to dryness under reduced pressure to give 88.5 g of phenylthioethyl 4-chloroacetoacetate as an oil.

The above oil (88.5 g) was dissolved in a mixture of 90 ml of ethyl acetate and 180 ml of glacial acetic acid. The solution was cooled to 5° C. or below and a solution of 28.5 g of sodium nitrite in 80 ml of water was added dropwise to the solution at 5° C. or below over a period of about 2 hours. The mixture was poured into 800 ml of water to for extraction. The aqueous layer was further extracted with 1 liter of ethyl acetate. The organic layers were combined, washed with 500 ml of 5% aqueous sodium hydrogen carbonate and concentrated under reduced pressure to give 89 g of phenylthioethyl 4-chloro-2-hydroxyiminoacetate as an oil.

The above oil (89 g) was dissolved in a mixture of 400 ml of ethanol and 40 ml of water, and 23 g of thiourea and 41.2 g of sodium acetate were added. The mixture was stirred at room temperature for 3 hours. After completion of the reaction, 400 ml of water was added and the mixture was cooled to 5° C. or below. The resulting crystalline precipitate was collected by filtration to give 40.1 g of phenylthioethyl 2-(2-aminothiazol-4-yl)-(Z)-2-hydroxyiminoacetate. Yield: 38.3% based on phenylthioethanol.

NMR (60 MHz, DMSO-$d_6$) δ: 3.40 (2H, t, J=8 Hz, C$\underline{H_2}$SC$_6$H$_5$), 4.40 (2H, t, J=8 Hz, —C$\underline{H_2}$CH$_2$S), 6.90 (1H. s, thiazole—5—H), 7.20–7.50 (7H, m, arom. and NH$_2$—).

IR $\nu_{max}^{KBr}$ cm$^{-1}$: 3400–2900, 1730, 1620, 1600, 1590, 1545.

EXAMPLE 23

(1) In 100 ml of acetone was suspended 5 g (0.0155 mole) of phenylthioethyl 2-(2-aminothiazol-4-yl)-(Z)-2-hydroxyiminoacetate as obtained in Example 22, and 0.3 ml of water, 4.5 g (0.023 mole) of t-butyl bromoacetate and 8.5 g of anhydrous potassium carbonate were added in that order. The reaction was allowed to proceed at 40° C. for 6 hours. After completion of the reaction, the insoluble matter was filtered off and 200 ml of ethyl acetate and 200 ml of water were added for effecting extraction. The organic layer was washed with 200 ml of 5% aqueous sodium chloride and dehydrated by addition of anhydrous sodium sulfate. The solvent was then distilled off under reduced pressure and 100 ml of ethyl acetate-isopropyl ether (1:5, v/v) was added to the residue. After cooling, the crystalline precipitate was collected by filtration to give 5.8 g (yield, 85.5%) of phenylthioethyl 2-(2-aminothiazol-4-yl)-(Z)-2-(t-butoxycarbonylmethoxyimino)acetate as white crystals.

Elemental analysis: Calcd. for C$_{19}$H$_{23}$N$_3$O$_5$S$_2$=437.53: C52.11%, H5.25%, N9.60%. Found: C52.08%, H5.29%, N9.11%.

NMR (60 MHz, DMSO-$d_6$) δ: 1.45 (9H, s, C(C$\underline{H_3}$)$_3$), 3.30 (2H, t, J=8 Hz, C$\underline{H_2}$SC$_6$H$_5$), 4.40 (2H, t, J=8 Hz, COOC$\underline{H_2}$), 4.60 (2H, s, OC$\underline{H_2}$CO), 6.95 (1H. s, thiazol$\underline{e}$—5—H), 7.20–7.50 (7H, m, arom. and NH$_2$—).

IR $\nu_{max}^{KBr}$ cm$^{-1}$: 3450–2950, 1740, 1620, 1590, 1545.

(2) In a mixture of 50 ml of acetone and 10 ml of water was dissolved 5.0 g (0.0114 mole) of phenylthioethyl 2-(2-aminothiazol-4-yl)-(Z)-2-(t-butoxycarbonylmethoxyimino)acetate as obtained in (1). To the solution was added 0.05 g of ammonium molybdate and, at 25°–30° C., 13 ml (0.115 mole) of 30% hydrogen peroxide was added. The reaction was allowed to proceed for 4 hours. The reaction mixture was poured into 500 ml of water and extracted with 500 ml of ethyl acetate. The organic layer was washed with 500 ml of 5% sodium sulfite and 500 ml of water in that order and concentrated to dryness. The residue was dissolved in a mixture of 200 ml of acetone and 50 ml of water, and a 40% potassium carbonate solution was added dropwise at 30°–35° C. at pH 10–11 for hydrolysis. The mixture was stirred for about 2 hours and 100 ml of water was added, followed by addition of 500 ml of ethyl acetate for extraction purification. The aqueous layer was adjusted to pH about 2 with 2N HCl, whereupon crystals separated out. The mixture was cooled to 5° C. or below and the crystalline precipitate was collected by filtration to give 2.57 g (yield, 74.8%) of 2-(2-aminothiazol-4-yl)-(Z)-2-(t-butoxycarbonylmethoxyimino)acetic acid as white crystals.

The NMR and IR spectra of this product were identical with those of the compound obtained in Example 16.

EXAMPLE 24

(1) Using 5 g (0.0156 mole) of phenylthioethyl 2-(2-aminothiazol-4-yl)-(Z)-2-hydroxyiminoacetate as obtained in Example 22 and 4.9 g (0.0234 mole) of t-butyl 2-bromopropionate and following the procedure (1) of Example 23, there was obtained 5.8 g (yield, 82.3%) of phenylthioethyl 2-(2-aminothiazol-4-yl)-(Z)-2-(t-butoxycarbonyl-1-methylmethoxyimino)acetate as white crystals.

Elemental analysis: Calcd. for C$_{20}$H$_{25}$N$_3$O$_5$S$_2$=451.55: C, 53.15%; H, 5.53%; N, 9.30%. Found: C, 53.30%; H, 5.50%; N, 9.07%.

NMR (60 MHz, DMSO-$d_6$) δ: 1.35 (3H, d, J=8 Hz, CHC$\underline{H_3}$), 1.41 (9H, s, C(C$\underline{H_3}$)$_3$), 3.28 (2H, t, J=8 Hz, C$\underline{H_2}$S), 4.40 (2H, t, J=8 Hz, C$\underline{H_2}$CH$_2$S), 4.60 (1H, q, J=8 Hz, C$\underline{H}$—CH$_3$), 6.90 (1H, s, thiazole—5—H) 7.20–7.50 (7$\overline{H}$, m, arom. and NH$_2$—).

IR $\nu_{max}^{KBr}$ cm$^{-1}$: 3400–2950, 1740, 1725, 1630, 1595, 1550.

(2) In the same manner as (2) of Example 23, 4.0 g (0.0089 mole) of phenylthioethyl 2-(2-aminothiazol-4-yl)-(Z)-2-(t-butoxycarbonyl-1-methylmethoxyimino)acetate as obtained in (1) was oxidized with aqueous hydrogen peroxide and then hydrolyzed in an alkaline condition adjusted with potassium carbonate. Adjustment of the pH to about 2 gave 2.0 g (yield, 71.3%) of 2-(2-aminothiazol-4-yl)-(Z)-2-(t-butoxycarbonyl-1-methylmethoxyimino)acetic acid as white crystals.

The NMR and IR data confirmed that this product was identical with the compound obtained in Example 20.

EXAMPLE 25

(1) Using 5 g (0.0156 mole) of phenylthioethyl 2-(2-aminothiazol-4-yl)-(Z)-2-hydroxyiminoacetate as obtained in Example 22 and 5.2 g (0.0233 mole) of t-butyl 2-bromoisobutyrate and following the procedure (1) of Example 23, there was obtained 6.0 g (yield, 82.6%) of phenylthioethyl 2-(2-aminothiazole-4-yl)-(Z)-2-(t-butoxycarbonyl-1,1-dimethylmethoxyimino) acetate as white crystals Elemental analysis: Calcd. for C$_{21}$H$_{27}$N$_3$O$_5$S$_2$=465.58: C54.13%, H5.80%, N9.02%. Found: C54.47%, H5.64%, N8.78%.

NMR (60 MHz, DMSO-d$_6$) δ: 1.40 (15H, s, C (CH$_3$)$_3$ and C (CH$_3$)$_2$), 3.30 (2H, t, J=8 Hz, CH$_2$S—), 4.40 (2H, t, J=8 Hz, COCH$_2$CH$_2$), 6.90 (1H, s, thiazole—5—H), 7.20–7.50 (7H, m, arom. and NH$_2$—).

IR ν$_{max}^{KBr}$ cm$^{-1}$: 3400–2950, 1740, 1710, 1630, 1590, 1545.

(2) In the same manner as (2) of Example 23, 5.0 g (0.0107 mole) of phenylthioethyl 2-(2-aminothiazol-4-yl)-(Z)-2-(t-butoxycarbonyl-1,1-dimethylmethoxyimino)acetate as obtained in (1) was oxidized with aqueous hydrogen peroxide and then hydrolyzed. Adjustment of the pH to about 2 gave 2.0 g (yield, 56.7%) of 2-(2-aminothiazol-4-yl)-(Z)-2-(t-butoxycarbonyl-1,1-dimethylmethoxyimino)acetic acid as white crystals.

The NMR and IR data confirmed that this product was identical with the compound obtained in Example 21.

EXAMPLE 26

In 140 ml of acetonitrile was suspended 5.42 g of 2-(2-aminothiazol-4-yl)-(Z)-2-(t-butoxycarbonylmethoxyimino)acetic acid as obtained in Example 4 followed by a serial addition of 2.96 ml of N-methylmorpholine and 7.2 g of 2,2-dithiobisbenzothiazole. The suspension was cooled to 0° C. and a solution of 5.38 ml of triethyl phosphite in 35 ml of acetonitrile was added to the suspension over a period of 4.5 hours. The mixture was stirred for 30 minutes and cooled to −10° C. or below. The resulting precipitate was collected by filtration, washed with 20 ml of cold acetonitrile and dried in vacuo at room temperature to give 6.2 g (yield, 76.5%) of s-(2-benzothiazolyl) 2-(2-aminothiazol-4-yl)-(Z)-2-(t-butoxycarbonylmethoxyimino)thioacetate as light-yellow crystals.

NMR (60 MHz, DMSO-d$_6$) δ: 1.47 (9H, s, C (CH$_3$)$_3$), 4.71 (2H, s, OCH$_2$CO) 7.05 (1H, s, thiazole 5—H), 7.39 (2H, s, NH$_2$), 7.45–7.62 (2H, m, arom), 8.00–8.28 (2H, m, arom).

IR (KBr) cm$^{-1}$: 3425, 3150, 1740, 1710, 1620, 1540.

REFERENCE EXAMPLE 1

(1) In 40 ml of tetrahydrofuran-water (4:1) was suspended 1.5 g of 7-amino-3-methylthiomethylcephem-4-carboxylic acid, and 1.6 ml of triethylamine was added at room temperature. Then, 2.86 g of thioester obtained in Example 26 was added to the suspension and the reaction was allowed to proceed at room temperature for 2 hours. After completion of the reaction, the solvent was distilled off and 50 ml of water was added to the residue. The mixture was washed with ethyl acetate and the washings were adjusted to pH about 2.5 with hydrochloric acid and extracted with 50 ml of ethyl acetate. The extract was dried over anhydrous sodium sulfate and the solvent was distilled off under reduced pressure. With ice-cooling, 20 ml of trifluoroacetic acid was added and the reaction was allowed to proceed for 2.5 hours. After completion of the reaction, the trifluoroacetic acid was distilled off under reduced pressure and water and 10% aqueous sodium hydrogen carbonate were added to the residue for dissolution. This solution was chromatographed on 200 ml of Amberlite XAD-II (manufactured by Rohm & Haas Co., U.S.A.), elution being carried out with water. The active fractions were combined and lyophilized to give 1.8 g of disodium 7β-[2-(2-aminothiazol-4-yl)-(Z)-2-(carboxymethoxyimino)acetamido]-3-methylthiomethyl-3-cephem-4-carboxylate as a white powder.

Elemental analysis: Calcd. for C$_{16}$H$_{15}$N$_5$O$_7$S$_3$Na$_2$.5-H$_2$O: C30.90%, H4.05%, N11.31%. Found: C30.95%, H3.86%, N11.26%.

NMR (60 MHz, D$_2$O) δ: 2.00 (3H, s, SCH$_3$), 3.10–3.95 (4H, m, methylene at position 2 and CH$_2$SCH$_3$), 4.56 (2H, s, =NOCH$_2$) 5.21 (1H, d, J=5 Hz, proton at potision 6), 5.75 (1H, d, J=5 Hz, proton at position 7), 7.03 (1H, s, thiazole 5—H).

IR (KBr) cm$^{-1}$: 3400, 1760, 1610, 1535.

(3) Using 7-amino-3-[(5-methyl-1,3,4-thiadiazol-2-yl)thiomethyl]-3-cephem-4-carboxylic acid and thioester obtained in Example 26, in the same manner as the above reaction procedure (1), disodium 7β-[2-(2-aminothiazol-4-yl)-(Z)-2-(carboxymethoxyimino)]acetamido-3-[(5-methyl-1,3,4-thiadiazol-2-yl)thiomethyl]-3-cephem-4-carboxylate was obtained.

Elemental analysis: Calcd.: C31.44%, H3.37%, N14.26%. Found: C31.50%, H3.37%, N13.48%.

NMR (60 MHz, D$_2$O) δ: 2.80 (3H, s, CH$_3$), 3.65 (2H, q, proton at position 2), 4.15 (2H, s, NOCH$_2$CO), 5.25 (1H, d, proton at position 6), 5.85 (1H, d, proton at position 7), 7.00 (1H, s, thiazole 5—H).

REFERENCE EXAMPLE 2

(1) In 140 ml of dry acetonitrile is suspended 5.42 g (18 mmol) of (Z)-2-(2-amino-4-thiazolyl)-2-(t-butoxycarbonylmethoxyimino)acetic acid, 2.96 ml (27 mmol) of N-methyl morpholine and then 7.2 g (21.6 mmol) of bis-benzothiazol-2-yl disulfide are added, and the mixture is cooled to 0° C. A solution of 5.38 ml (31:4 mmol) of triethyl phosphite in 35 ml of dry acetonitrile is added dropwise over 4.5 hours and the mixture is stirred at the same temperature for 30 minutes and then cooled to −10° C. The resulting crystalline precipitate is collected by filtration, washed with a small amount of acetonitrile and dried under reduced pressure to give 5.1 g of (Z)-2-(2-amino-4-thiazolyl)-2-(t-butoxycarbonylmethoxyimino)acetic acid 2-benzothiazolylthiol ester.

IR ν (KBr) cm$^{-1}$: 3400, 3120, 1738, 1710, 1620, 1540, 1450, 1415, 1370.

NMR (d$_6$-DMSO) δ: 1.50 (9H, s, CH$_3$×3), 4.78 (2H, s, NOCH$_2$COO), 7.10 (1H, s, thiazole-5H), 7.4–7.65 (2H, m, aromatic protons), 8.0–8.3 (2H, m, aromatic protons).

(2) A flask of 1.0 l capacity is charged with 0.06 kg (0.2508 mole) of (3S,4S)-3-amino-4-carbamoyloxymethyl-2-azetidinone-1-sulfonic acid and 0.9 l of methylene chloride to make a suspension, 0.070 l (0.2508×2 mol) of triethylamine and then 0.124 kg (0.2508×1.1 mol) of (Z)-2-(2-amino-4-thiazolyl-2-t-butoxycarbonylmethoxyimino)acetic acid 2-benzothiazolylthio ester obtained in (1) are added to the suspension under stirring at 10°–20° C., and the mixture is stirred at 25°–27° C. for 4 hours. The insoluble matter is filtered off and the filtrate is further stirred for about an hour and extracted with 0.9 l of water. The aqueous layer is washed with 0.19 l of methylene chloride, 0.38 l of ethyl acetate and 0.19 l of methylene chloride in that order. After degassing, 0.45 l of concentrated hydrochloric acid is added and the mixture is stirred at 25° C. for about 2 hours. To the resulting slurry is added 0.9 l of water and the mixture is stirred at about 25° C. for about 2 hours and then allowed to stand at 0°–2° C. overnight. The resulting precipitates are collected by filtration and washed with about 0.6 l of cold water to give about 0.27 kg of (3S, 4S)-3-[2-(2-amino-4-thiazolyl)-(Z)-2-(carboxymethoxyimino)acetamido]-4-carbamoyloxymethyl-2-acetidinone-1-sulfonic acid as wet crystals.

$[\alpha]_D^{26}$ −45° (c=1, DMSO).

IR $\nu_{max}^{KBr}$ cm$^{-1}$: 1760, 1715, 1670, 1640.

NMR (d$_6$-DMSO) δ: 3.9–4.4 (3H, C$_4$—H, C$_4$—CH$_2$), 4.66 (2H, s, NO—CH$_2$), 5.28 (1H, d.d, J=4.5, 10 Hz, C$_3$—H), 6.92 (1H, s, proton at position 5 of the thiazole nuclear), 9.33 (1H, d, J=10 Hz, C$_3$—NH).

Antimicrobial potency (MIC) against *K. pneumoniae* TN 1711: 0.1 mcg/ml.

What we claim is:

1. A process of producing an aminothiazoleacetic acid derivative of the formula

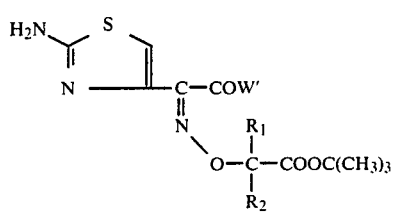

wherein R$_1$ and R$_2$ each is hydrogen or lower alkyl; and W' is hydroxyl or 2-benzothiazolylthio, or a salt thereof, which comprises reacting diketene with a halogen, reacting the resulting 4-haloacetoacetyl halide with an alcohol of the formula

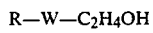

wherein R is lower alkyl or phenyl; and W is S or SO$_2$, reacting the resulting compound of the formula

wherein X is halogen; and R and W are as defined above, with nitrous acid, or a salt thereof, reacting the resulting compound of the formula

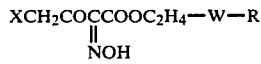

wherein the symbols are as defined above, with thiourea or a salt thereof, reacting the resulting compound of the formula

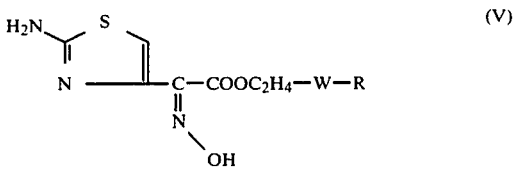

wherein the symbols are as defined above, or a salt thereof, with a compound of the formula

wherein X' is halogen; and R$_1$ and R$_2$ are as defined above, oxidizing the reaction product when W is S, and (i) hydrolyzing the compound thus obtained of the formula

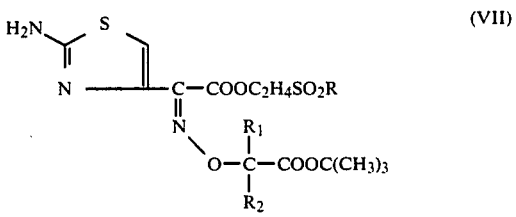

wherein the symbols are as defined above, or a salt thereof, in the presence of a base, or (ii) hydrolyzing the compound (VII) or a salt thereof in the presence of a base, and reacting the resulting product with 2,2-dithiobis-benzothiazole.

2. A process according to claim 1, wherein R$_1$ and R$_2$ both are hydrogen.

3. A process according to claim 1, wherein R is lower alkyl.

4. A process according to claim 1, wherein W is S.

5. A process according to claim 1, wherein W' is hydroxyl.

6. A process according to claim 1, wherein W' is 2-benzothiazolylthio.

* * * * *